United States Patent
Gray

[11] Patent Number: 5,921,945
[45] Date of Patent: *Jul. 13, 1999

[54] SPLINT/THERAPEUTIC DEVICE

[76] Inventor: James C. Gray, 2405 Alcoa Hwy., Knoxville, Tenn. 37920

[*] Notice: This patent is subject to a terminal disclaimer.

[21] Appl. No.: 08/559,159

[22] Filed: Nov. 13, 1995

[51] Int. Cl.⁶ .................................. A61F 5/00; A61F 5/37
[52] U.S. Cl. ................................. 602/5; 602/20; 602/21; 128/882
[58] Field of Search .................................. 602/5, 6, 7, 8, 602/12, 20, 21, 22, 23, 26; 128/845, 846, 882, 877, 878

[56] References Cited

U.S. PATENT DOCUMENTS

| | | |
|---|---|---|
| 1,716,221 | 6/1929 | Fernie . |
| 1,726,728 | 9/1929 | Adams . |
| 3,117,786 | 1/1964 | Anderson .................................. 273/54 |
| 3,152,337 | 10/1964 | Barry .......................................... 2/159 |
| 3,555,564 | 1/1971 | Miskell et al. .............................. 2/168 |
| 3,581,740 | 6/1971 | Sherbourne . |
| 3,605,120 | 9/1971 | Hobbs ......................................... 2/159 |
| 3,779,550 | 12/1973 | Benoun et al. ......................... 273/54 B |
| 3,788,307 | 1/1974 | Kistner . |
| 3,903,878 | 9/1975 | Spann . |
| 3,911,497 | 10/1975 | Lewis, Jr. et al. ............................. 2/16 |
| 3,944,220 | 3/1976 | Fasano ....................................... 272/67 |
| 4,041,940 | 8/1977 | Frankel et al. . |
| 4,167,044 | 9/1979 | Girard ............................................. 3/1 |
| 4,173,218 | 11/1979 | Cronin . |
| 4,183,098 | 1/1980 | Knowles, Jr. .................................. 2/16 |
| 4,417,570 | 11/1983 | Finnieston . |
| 4,451,044 | 5/1984 | Elliot, Jr. ............................. 273/189 A |
| 4,558,694 | 12/1985 | Barber . |
| 4,565,195 | 1/1986 | Eisenberg . |
| 4,573,456 | 3/1986 | Spann . |
| 4,675,914 | 6/1987 | Mitchell .................................. 2/161 A |
| 4,698,850 | 10/1987 | Patton, Sr. et al. .......................... 2/159 |
| 4,716,892 | 1/1988 | Brunswick . |
| 4,719,906 | 1/1988 | DeProspero . |
| 4,765,319 | 8/1988 | Finnieston et al. . |
| 4,781,178 | 11/1988 | Gordon . |
| 4,787,376 | 11/1988 | Eisenberg . |
| 4,798,199 | 1/1989 | Hubbard et al. . |
| 4,807,609 | 2/1989 | Meals . |
| 4,883,073 | 11/1989 | Aziz . |
| 4,911,150 | 3/1990 | Farley . |
| 4,925,187 | 5/1990 | Fleenor et al. ......................... 273/54 B |
| 4,945,925 | 8/1990 | Garcia . |
| 4,960,114 | 10/1990 | Dale . |
| 4,977,890 | 12/1990 | Mann . |

*Primary Examiner*—Richard J. Apley
*Assistant Examiner*—Kim M. Lee
*Attorney, Agent, or Firm*—Pitts & Brittian, P.C.

[57] ABSTRACT

An improved splint/therapeutic device for at least partially immobilizing a portion of a patient's body. The device includes a splint body fabricated of a resilient material, the splint body defining an inner surface for engaging the patient's body. The splint body also defines a preselected flexibility whereby the resilient material of the splint body biases the patient's body to a desired body position and provides a preselected degree of mobility.

24 Claims, 22 Drawing Sheets

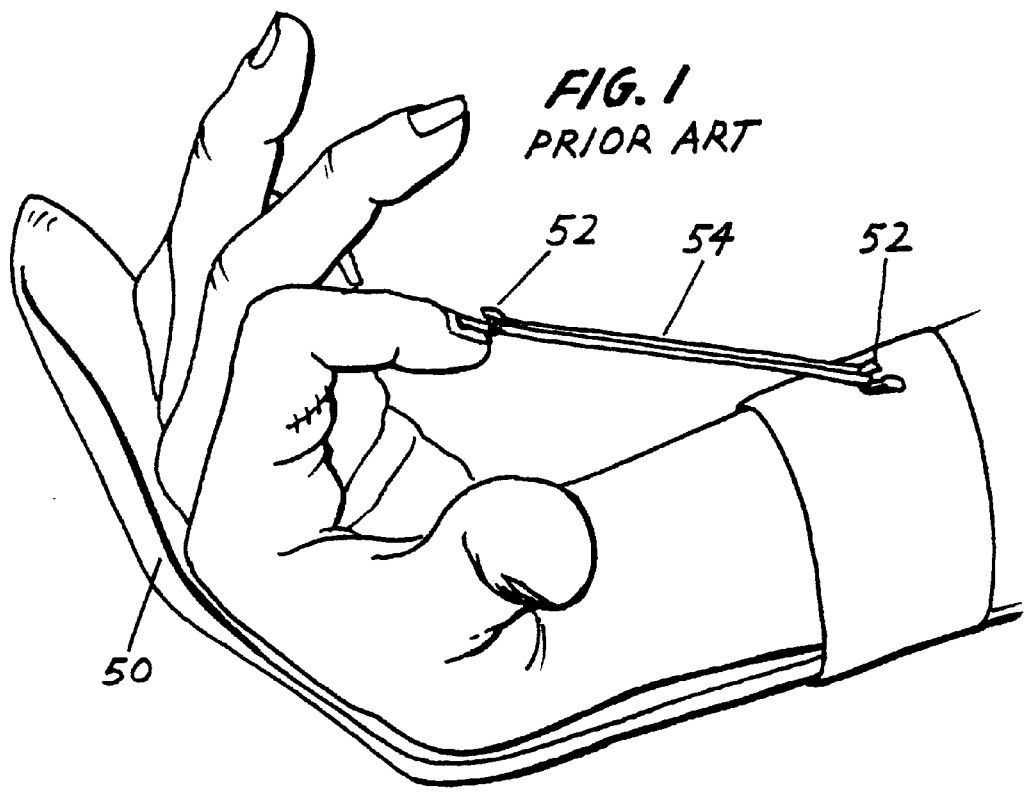
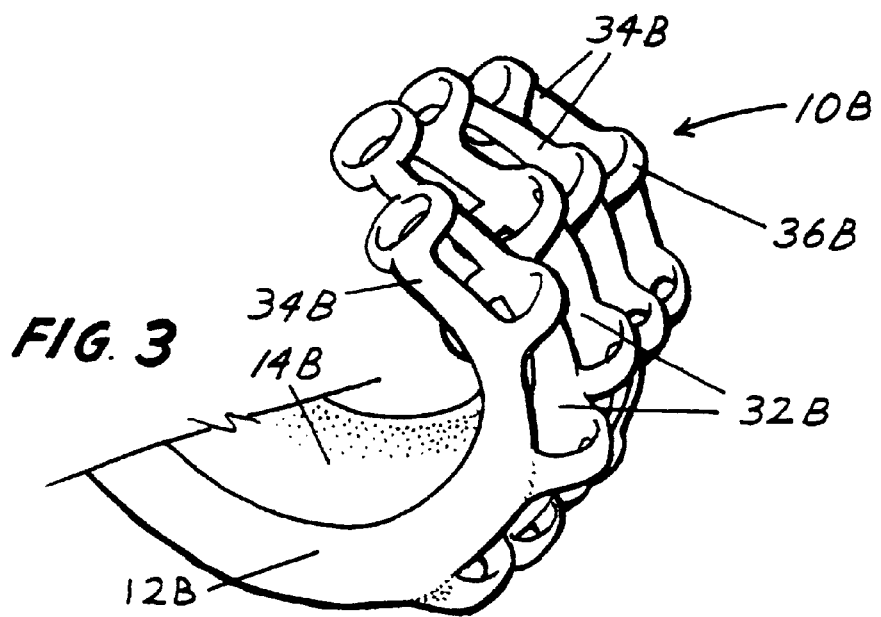

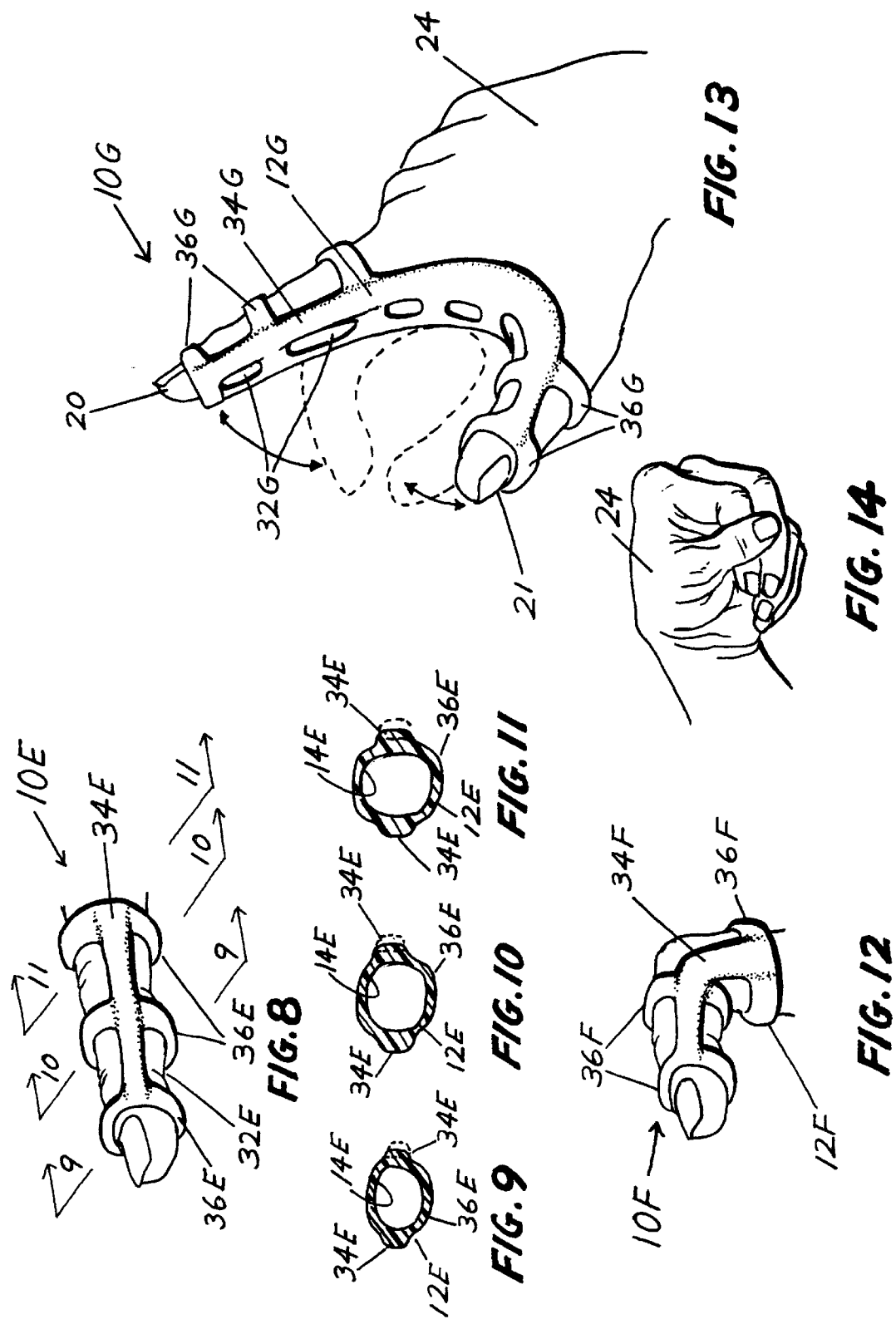

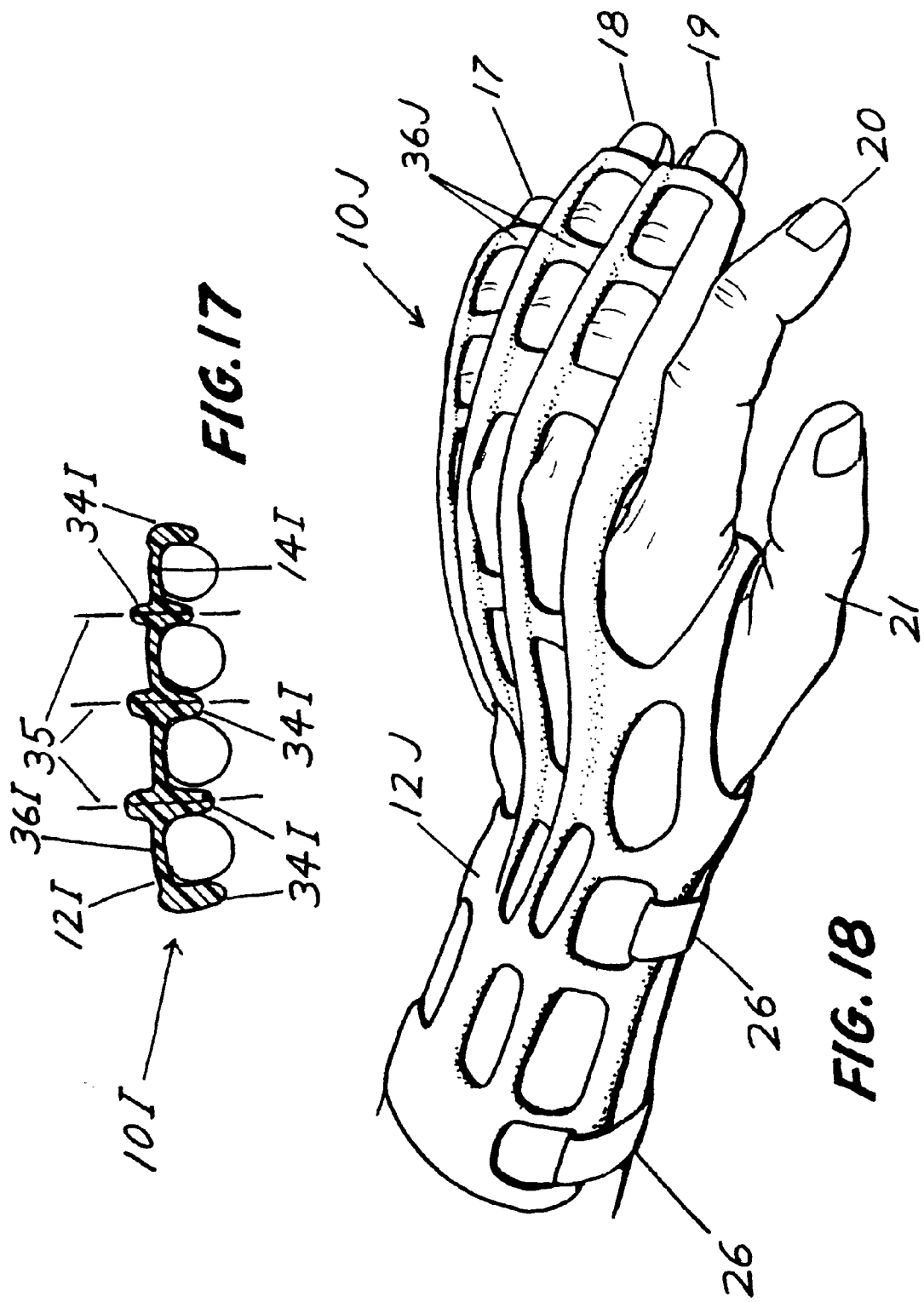

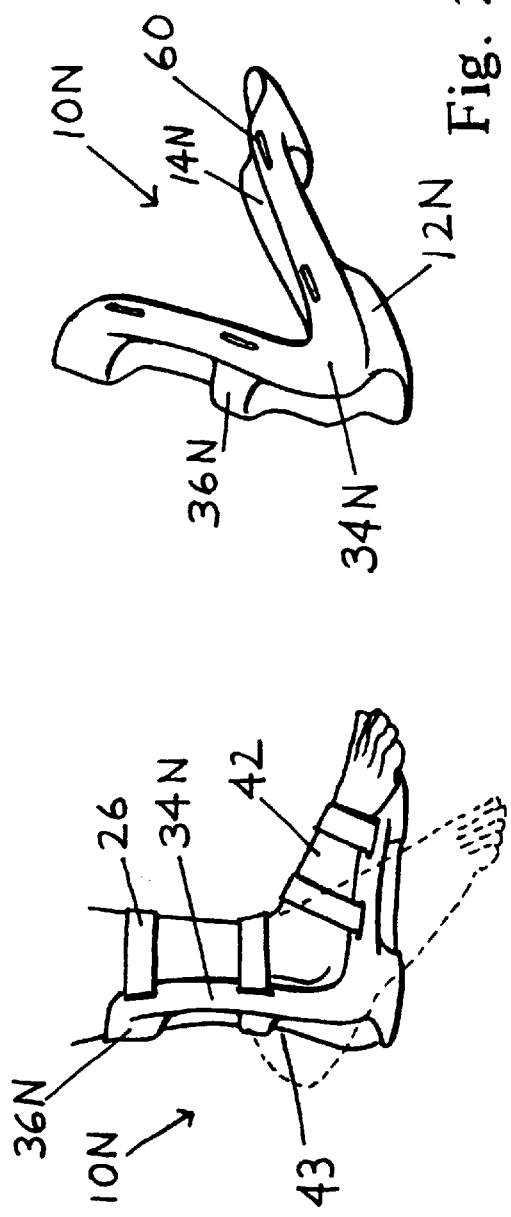

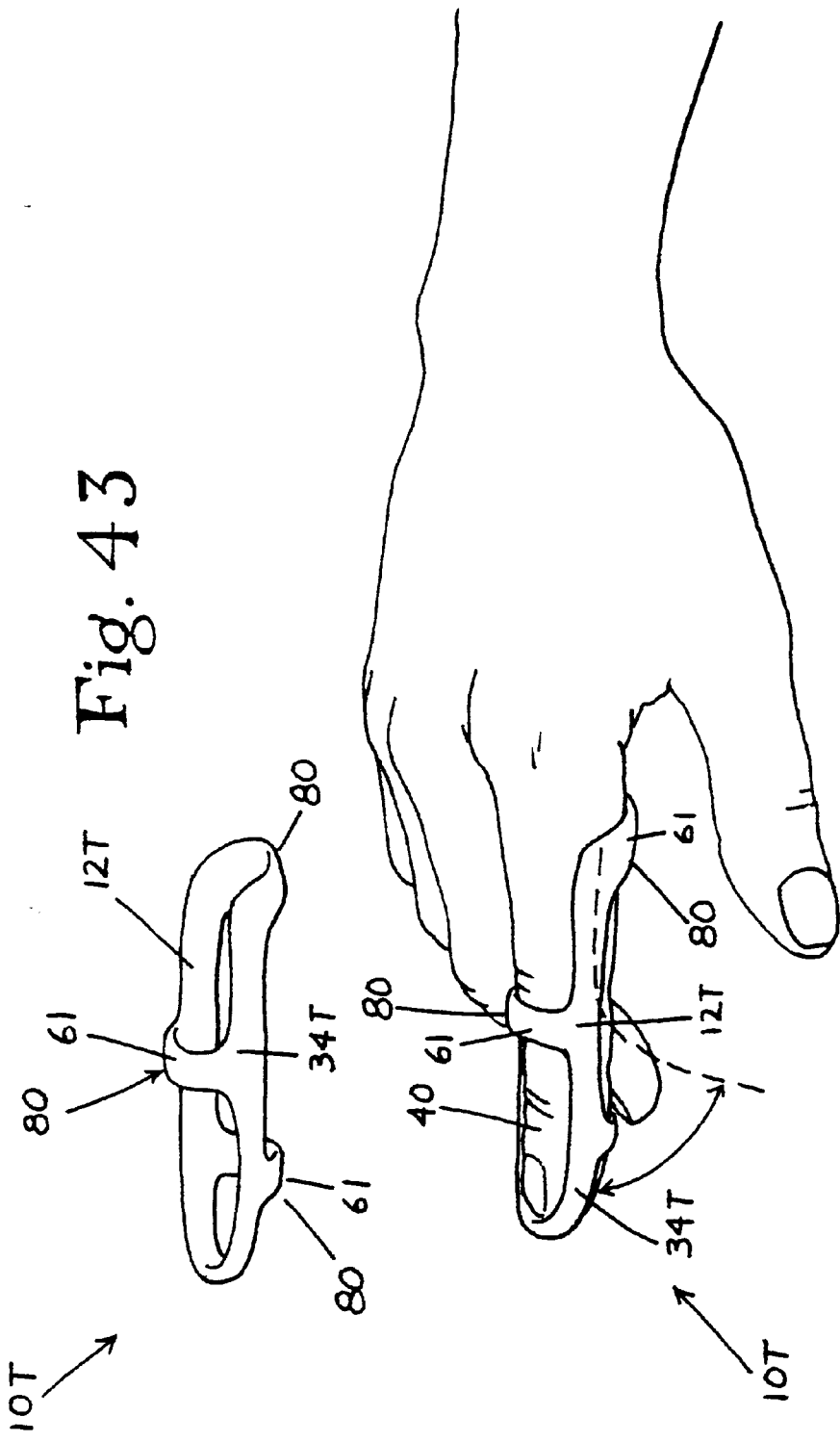

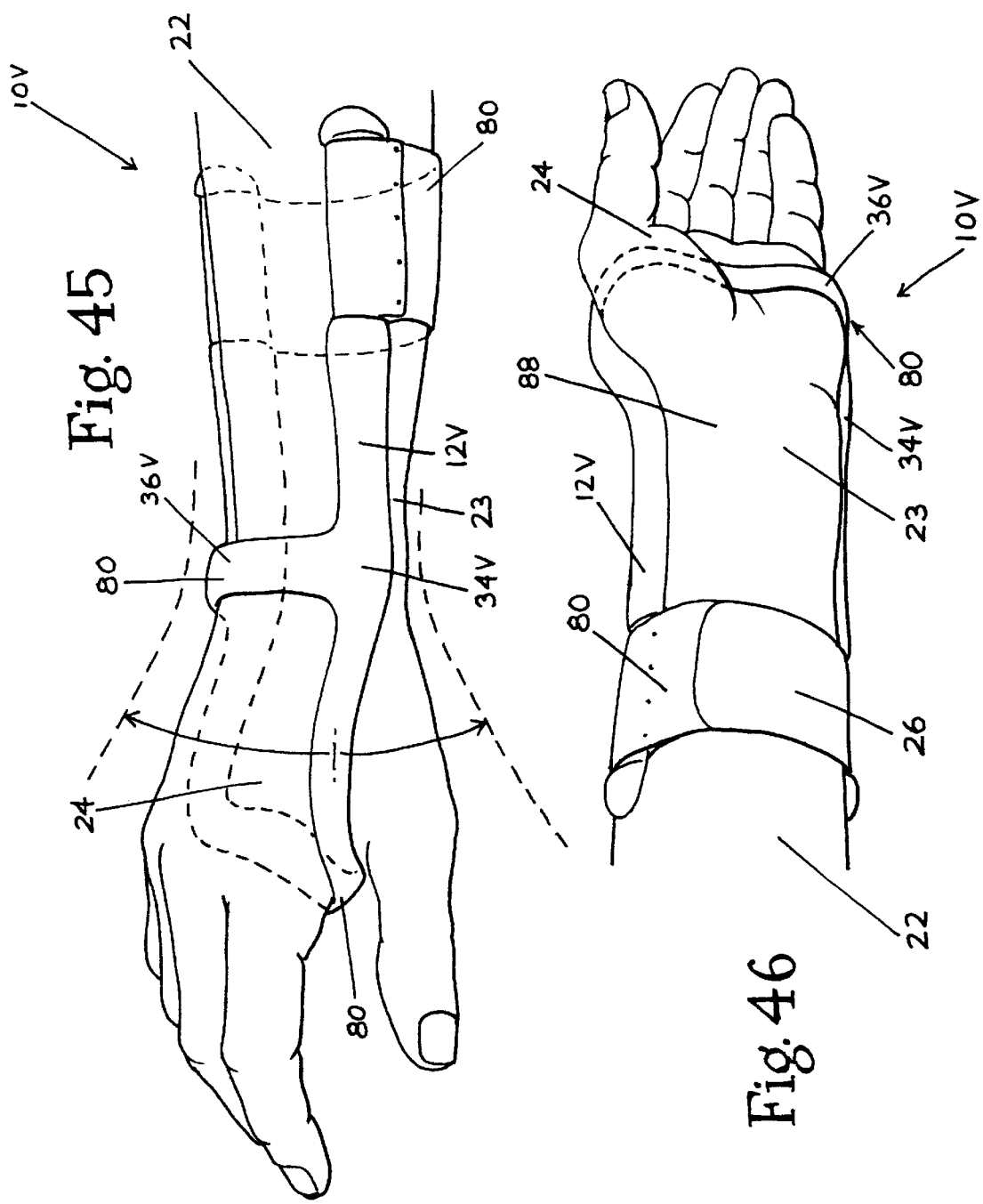

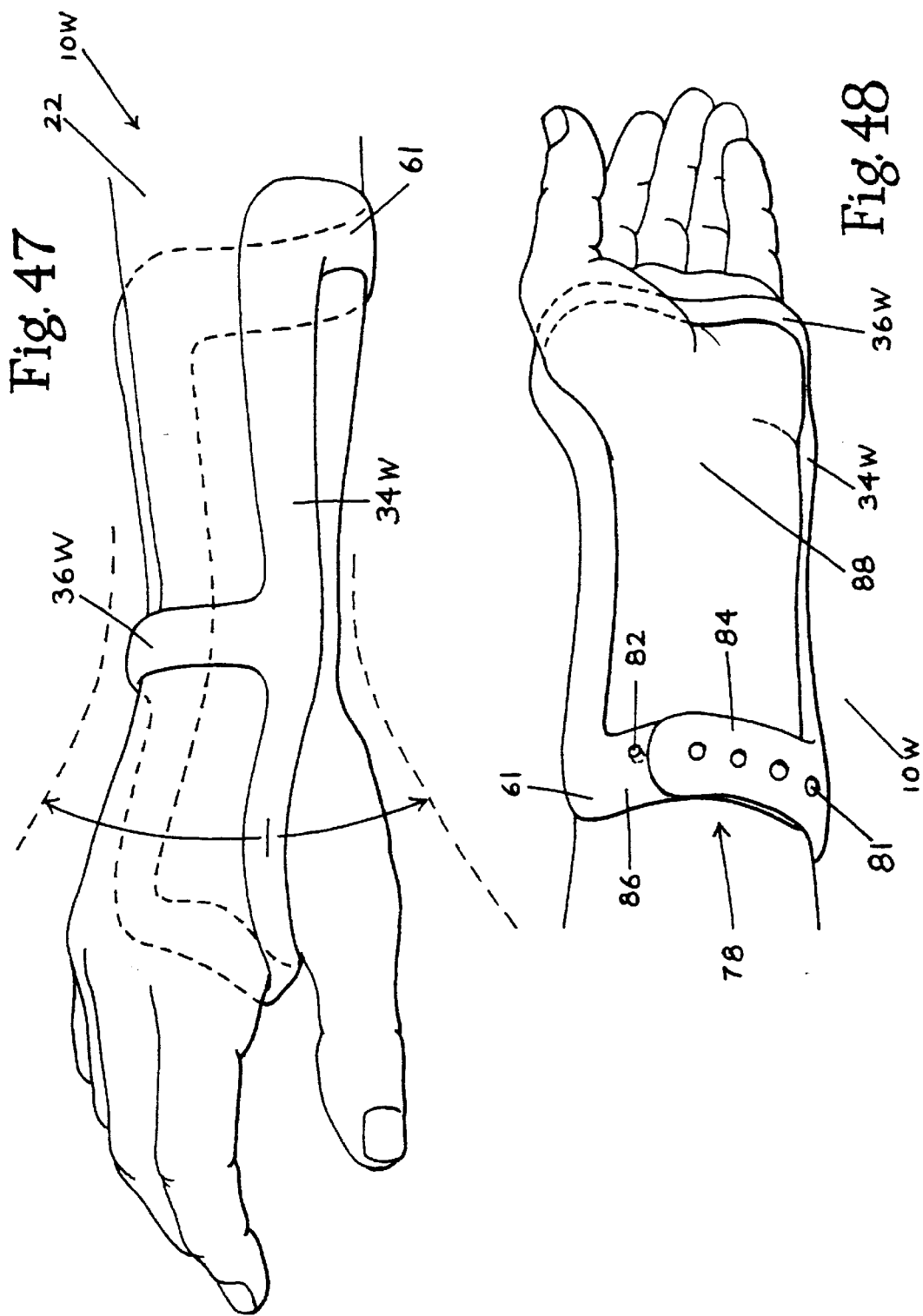

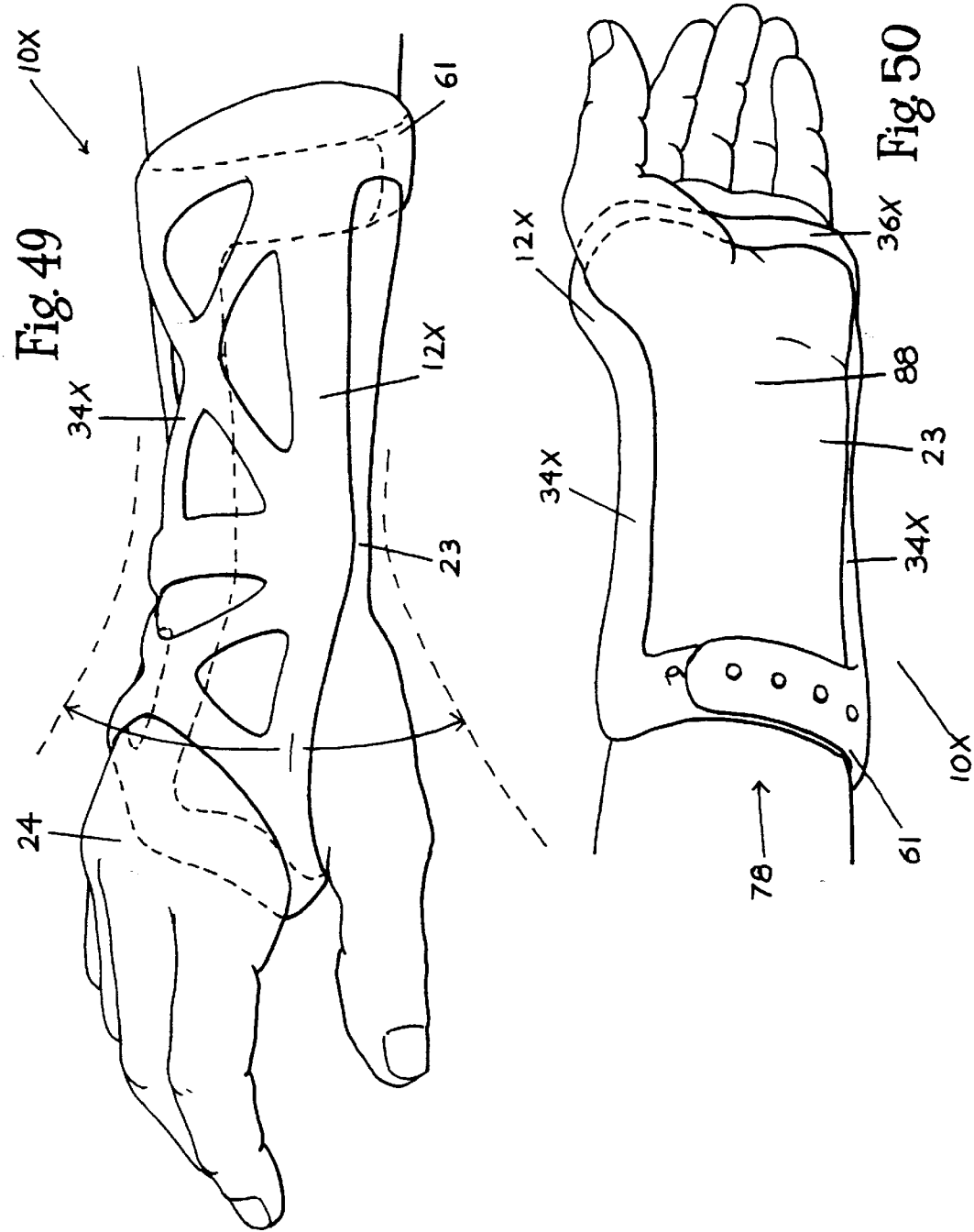

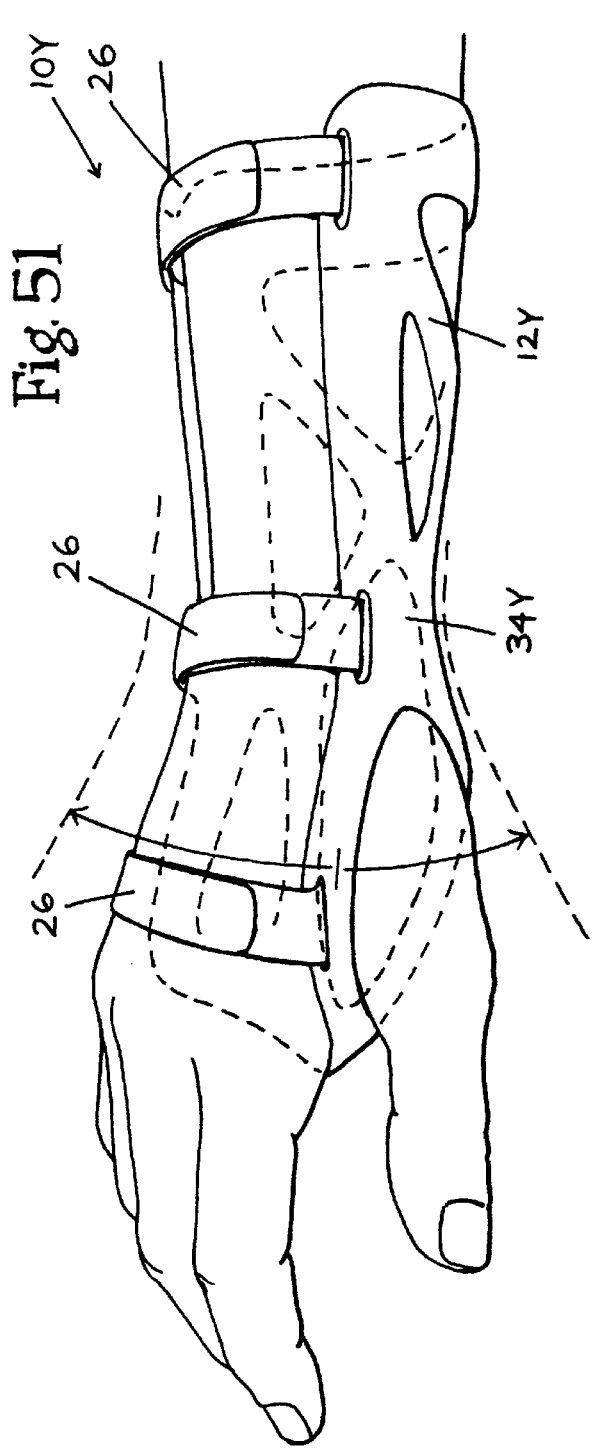
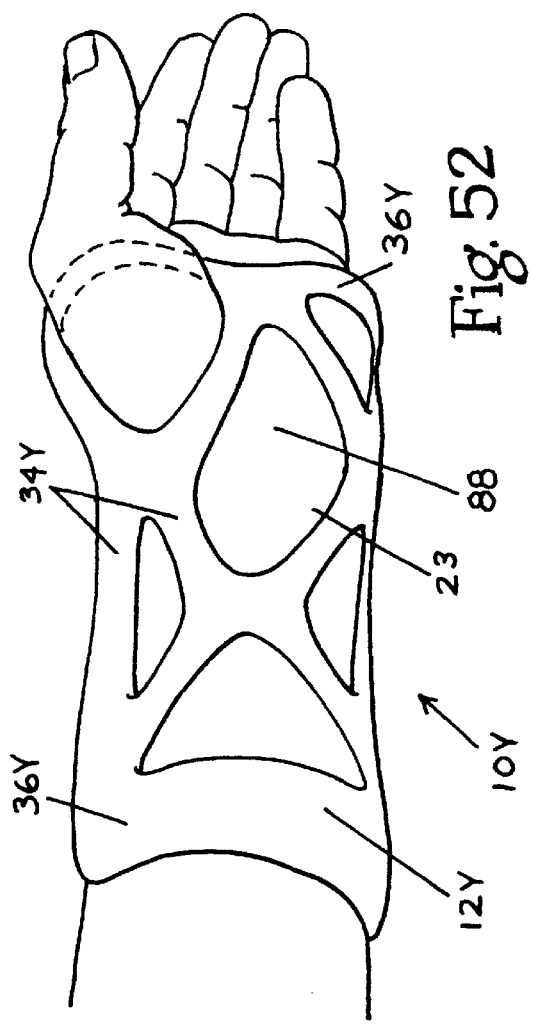

SPLINT/THERAPEUTIC DEVICE

This application in part discloses and claims subject matter disclosed in my earlier filed pending application, Ser. No. 08/178,841, filed Jan. 7, 1994, which is a continuation-in-part application of my earlier filed application, Ser. No. 07/947,938, filed Sep. 21, 1992, which is a continuation-in-part application of my earlier filed application, Ser. No. 07/633,128, filed Dec. 24, 1990, now abandoned, which is a continuation-in-part application of my earlier filed application, Ser. No. 07/405,657, filed Sep. 11, 1989, now abandoned.

TECHNICAL FIELD

This invention relates to an improved splint and therapeutic device for at least partially immobilizing selected portions of a patient's body. In this particular invention, the splint includes an integrally molded elastomeric body which selectively varies in thickness. The splint may be used to bias a body portion—such as a hand, a finger, a foot, a toe, a knee, a leg, an arm, an elbow, the back, the neck, or the hips—to a preselected position to aid in the healing and rehabilitation process after injury, surgery, or the like, or to assist a patient with at least partially deteriorated muscle control.

BACKGROUND ART

Splints and casts have long been used to immobilize body joints, or the ends of fractured bones. However, conventional splints and casts are generally rigid devices which are secured to the body proximate the point of an injury, and result in total immobilization of the area to which they are applied, even if total immobility is unnecessary. For example, a cast or splint applied to immobilize a fracture in the wrist quite often needlessly immobilizes the patient's fingers and/or thumb, or a cast or splint applied to immobilize a fractured bone in the forearm may needlessly result in total immobilization of the elbow joint. Moreover, for some types of injuries or deformities, total immobilization is not desirable. For example, where a hand has been deformed by osteoarthritis, it is desirable to reorient the hand to bring it to the appropriate disposition, but not desirable to totally immobilize the hand. Attempts have been made to construct splints which do allow some residual mobility such as those disclosed in U.S. Pat. Nos. 4,719,906 issued to R. DeProspero on Jan. 19, 1988; and 4,781,178 issued to K. M. Gordon on Nov. 1, 1988. However, such splint devices tend to be complex and provide little selectivity as to the extent of mobility allowed the portion of the body to which they are applied. Other splints and similar devices are disclosed in the following U.S. Letters Patent:

| U.S. Pat. No. | Patentee(s) | Issue Date |
|---|---|---|
| 1,716,221 | T. R. Fernie | June 4, 1929 |
| 1,726,728 | W. G. Adams | Sept. 3, 1929 |
| 3,117,786 | J. H. Anderson | Jan. 14, 1964 |
| 3,152,337 | G. D. Barry | Oct. 13, 1964 |
| 3,555,564 | E. Miskell, et al. | Jan. 19, 1971 |
| 3,581,740 | R. D. Sherbourne | June 1, 1971 |
| 3,605,120 | H. B. Hobbs | Sept. 20, 1971 |
| 3,779,550 | S. M. Benoun, et al. | Dec. 18, 1973 |
| 3,788,307 | H. M. Kistner | Jan. 29, 1974 |
| 3,903,878 | D. C. Spann | Sept. 9, 1975 |
| 3,911,497 | F. H. Lewis, Jr., et al. | Oct. 14, 1975 |
| 3,944,220 | T. Fasano | Mar. 16, 1976 |
| 4,041,940 | S. A. Frankel, et al. | Aug. 16, 1977 |
| 4,167,044 | L. E. Girard | Sept. 11, 1979 |
| 4,173,218 | P. S. Cronin | Nov. 6, 1979 |
| 4,183,098 | M. V. Knowles, Jr. | Jan. 15, 1980 |
| 4,417,570 | A. Finnieston | Nov. 29, 1983 |
| 4,451,044 | D. D. Elliot, Jr. | May 29, 1984 |
| 4,558,694 | L. M. Barber | Dec. 17, 1985 |
| 4,565,195 | J. H. Eisenberg | Jan. 21, 1986 |
| 4,573,456 | D. C. Spann | Mar. 4, 1986 |
| 4,675,914 | R. Mitchell | June 30, 1987 |
| 4,698,850 | E. E. Patton, Sr., et al. | Oct. 13, 1987 |
| 4,716,892 | S. Brunswick | Jan. 5, 1988 |
| 4,765,319 | A. Finnieston, et al. | Aug. 23, 1988 |
| 4,787,376 | J. H. Eisenberg | Nov. 29, 1988 |
| 4,798,199 | V. M. Hubbard, et al. | Jan. 17, 1989 |
| 4,807,609 | R. A. Meals | Feb. 28, 1989 |
| 4,883,073 | F. Aziz | Nov. 28, 1989 |
| 4,911,150 | M. D. Farley | Mar. 27, 1990 |
| 4,925,187 | C. R. Fleenor, et al. | May 15, 1990 |
| 4,954,925 | R. F. Garcia | Aug. 7, 1990 |
| 4,960,114 | C. L. Dale | Oct. 2, 1990 |
| 4,977,890 | D. B. Mann | Dec. 18, 1990 |

A number of these patents disclose devices which may be used for purposes other than therapy, rehabilitation, and/or aiding the physically impaired. For example, those patents issued to Fernie ('221), Adams ('728), Anderson ('786), Barry ('337), Hobbs ('120), Benoun ('550), Lewis ('497), Knowles ('098), Elliot ('044), Eisenberg ('195 and '376), Mitchell ('914), and Fleenor ('187) disclose devices to be used in particular sports in order to prevent injury. Each of these either provides for the rigid support of a portion of the body—typically the hand or foot—or provides a cushioning means for reducing the force of a blow which might otherwise cause physical damage. The Miskell ('564) patent discloses a glove for use by a surgeon, while the Garcia ('925) patent discloses a device for aiding in the placement of an intravenous tube into a patient.

Of the remaining patents which are related primarily to therapy, rehabilitation, and/or aiding the physically impaired, none discloses a device which may define varying flexibilities over the body thereof. Further, none provides for the retention of the body portion in a preselected position until force is exerted upon the device in an attempt to move the body portion.

Such devices are desirable especially with cerebral palsy patients, patients who have suffered strokes, persons who have had tendon surgery and persons who suffer from or are susceptible to carpal tunnel syndrome. For many palsy patients, their hands are normally spasmed shut, and though they have muscular strength, they do not have the strength to open their hands. The same is true for stroke and arthritis patients. When held in the open position, however, the patient has the strength to close his hand, thereby allowing for the grasping and carrying of selected objects. By allowing such activity, many of these patients would be able function more normally, such as by feeding and clothing themselves.

For those recuperating from tendon surgery, such devices would also be desirable. Tendon surgery requires the tedious connection of the separated tendons and the careful stitching of the opening on the skin. Depending upon the function of the particular tendon, the associated digit or extremity must be retained in either the flexed or the contracted state in order to allow for better healing. As the healing process continues, more exercise may be accomplished without damage to the tendon. Conversely, exercise of the tendon will enhance the healing by preventing collagen formation and excessive scarring.

Typically, rigid casts and/or splints are used such as those disclosed in the cited prior art. These do not provide for the progressively increased exercise of the tendon. Devices such as casts do not allow for the observation of the healing process, as they are time consuming to remove and replace.

Also, the devices would be desirable to prevent the onset of carpal tunnel syndrome and relief for those suffering from carpal tunnel syndrome. Carpal tunnel syndrome is caused by compression of a major sensorimotor nerve at the wrist usually due to inflammation. To prevent or relieve carpal tunnel syndrome, the wrist needs to be supported in a particular manner to prevent or relieve the compression of the nerve. Because of the flexibility of the device, the patient will be able to function while maintaining the wrist in the preselected position. Current braces utilize a metal strip along the bottom of the arm and curved to the palm and fabric wrapping to immobilize the wrist. These put pressure on the problem area.

Therefore, an object of the present invention is to provide an improved splint/therapeutic device for at least partially immobilizing a portion of the body of a patient.

Another object of the present invention is to provide an improved splint/therapeutic device which allows the extent of immobility imparted to be preselected, and which allows such preselected extent of immobility to be varied over the surface area covered by the splint.

A further object of the present invention is to provide an improved splint/therapeutic device which is fabricated of an elastomeric material such that it can be trimmed to engage only that surface area of the patient's body where mobility is to be restricted.

Still another object of the present invention is to provide a splint/therapeutic device which defines a thickness that may be selectively thinned in order to allow for greater flexibility at subsequent stages in the healing process, thereby preventing the need for purchasing several devices to accomplish complete recovery.

Yet another object of the present invention is to provide an improved splint/therapeutic device which can also be used as a resistive exercise means.

Still a further object of the present invention is to provide an improved splint/therapeutic device which is inexpensive to manufacture.

DISCLOSURE OF THE INVENTION

Other objects and advantages will be accomplished by the present invention which provides an improved splint/therapeutic device for at least partially immobilizing a portion of the body of a patient and/or resistively exercising portions of a patient's body. The splint/therapeutic device comprises a splint body fabricated of a elastomeric material, the splint body having an inner surface for closely engaging a portion of the patient's body. Further, the splint body has a preselectively varying thickness, whereby the resistance to movement of the patient's body is correspondingly varied over the surface area of the body covered by the splint. The improved splint/therapeutic device also includes a suitable securing means for securing the splint on the body of the patient. In one preferred embodiment, such securing means includes adjustable securing straps which are received about the splint body and about the portion of the patient's body to which the splint is applied, and secured with hook-and-loop type fasteners.

BRIEF DESCRIPTION OF THE DRAWINGS

The above-mentioned features of the present invention will become more clearly understood from the following detailed description of the invention read together with the drawings in which:

FIG. 1 is a side elevational view of a prior art device used as a splint/therapeutic device;

FIG. 3 is a perspective view of an alternate embodiment of an improved splint/therapeutic device of the present invention;

FIG. 8 is a perspective view of an alternate embodiment of an improved splint/therapeutic device of the present invention;

FIG. 9 is an end view, in section, of the alternate embodiment of the improved splint/therapeutic device of the present invention as illustrated in FIG. 8;

FIG. 10 is an end view, in section, of the alternate embodiment of the improved splint/therapeutic device of the present invention as illustrated in FIG. 8;

FIG. 11 is an end view, in section, of the alternate embodiment of the improved splint/therapeutic device of the present invention as illustrated in FIG. 8;

FIG. 12 is a perspective view of an alternate embodiment of an improved splint/therapeutic device of the present invention;

FIG. 13 is a perspective view of an alternate embodiment of an improved splint/therapeutic device of the present invention;

FIG. 14 is a perspective view of a human hand which is spasmed in the closed position;

FIG. 17 is an end view, in section, of the alternate embodiment of the improved splint/therapeutic device of the present invention as illustrated in FIG. 16;

FIG. 18 is a perspective view of an alternate embodiment of an improved splint/therapeutic device of the present invention;

FIG. 25 is a perspective view of an alternate embodiment of an improved splint/therapeutic device of the present invention;

FIG. 26 is a perspective view of the alternate embodiment of the improved splint/therapeutic device of FIG. 25;

FIG. 27 is a perspective view of an elastomeric stiffener;

FIG. 28 is a perspective view of a gusset;

FIG. 43 is a perspective view of an alternate embodiment of an improved splint/therapeutic device of the present invention;

FIG. 44 is a perspective view of the alternate embodiment of an improved splint/therapeutic device of FIG. 43;

FIG. 45 is a perspective view of an alternate embodiment of an improved splint/therapeutic device of the present invention;

FIG. 46 is a bottom view of the alternate embodiment of FIG. 45;

FIG. 47 is a perspective view of the splint/therapeutic device of FIG. 45 with a molded strap;

FIG. 48 is a bottom view of the embodiment of FIG. 47;

FIG. 49 is a perspective view of an alternate embodiment of the splint/therapeutic device of the present invention;

FIG. 50 is a bottom view of the device of FIG. 49

FIG. 51 is an alternate embodiment of the splint/therapeutic device of the present invention; and, FIG. 52 is a bottom view of the splint of FIG. 51.

BEST MODE FOR CARRYING OUT THE INVENTION

Figure 2:
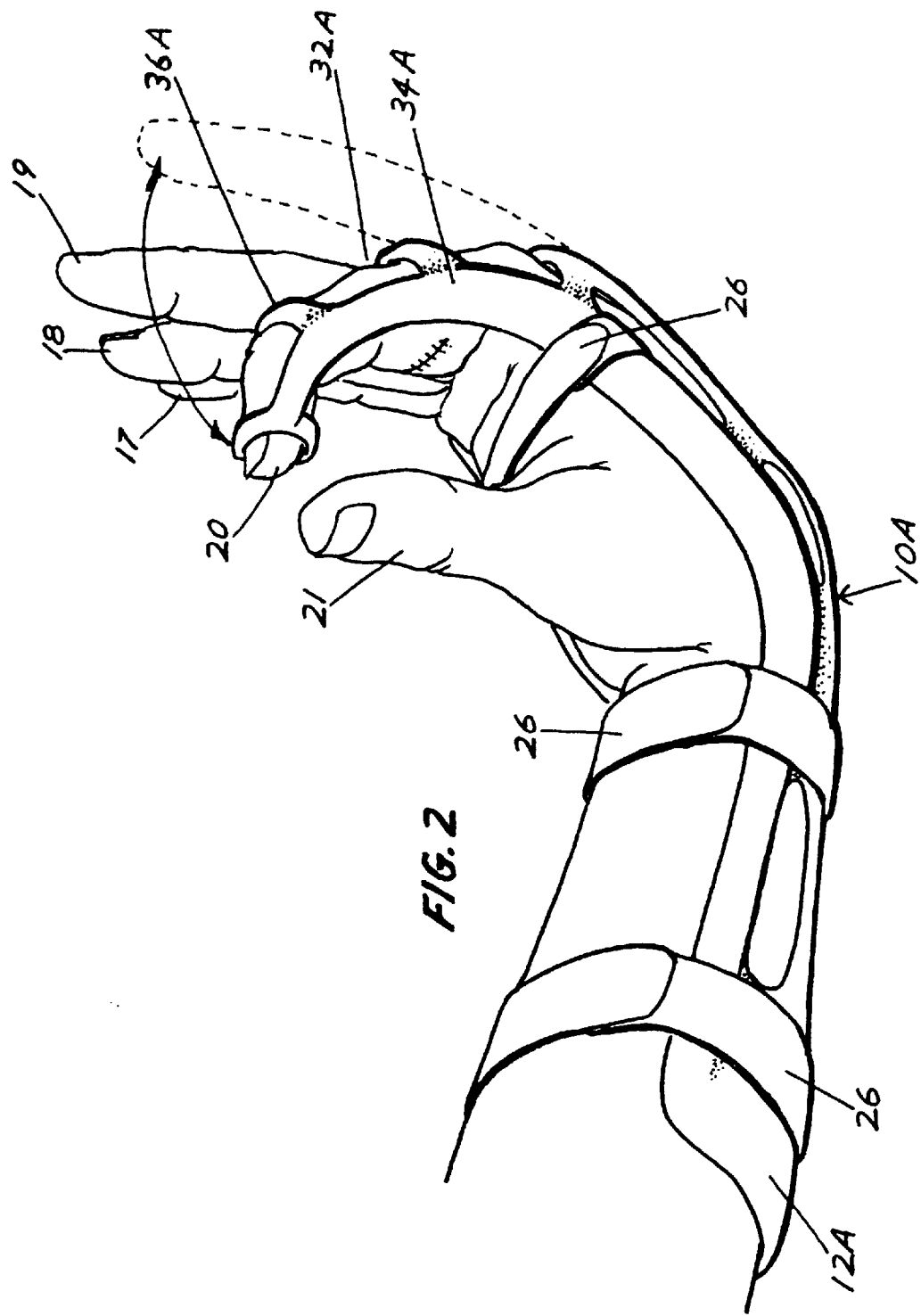
FIG. 2 is a perspective view of an alternate embodiment of an improved splint/therapeutic device of the present invention.

An improved splint/therapeutic device incorporating various features of the present invention is illustrated generally at 10 in the figures. The splint 10 of the present invention is designed to partially or totally immobilize a portion of a patient's body, and/or to provide resistive exercise for muscle or tendon therapy to that portion of the patient's body. The splint 10 is designed to replace prior art devices such as that shown in FIG. 1, wherein hooks 52 are affixed to a fingernail and a portion of the brace 50. A rubber band 54 is then stretched between the hooks 52 in order to prevent the finger from opening. This and other apparatuses may cause undue pain to the patient, or may otherwise be an unnecessary nuisance.

The splint 10 generally comprises a resilient splint body 12 which has an interior surface 14 for engaging a portion of the body of a patient. Preferably the splint body 12 is integrally molded of an elastomeric material, such as silicone rubber. Moreover, the splint body 12 is preferably molded such that the inner surface 14 is contoured, without the necessity of deformation through the application of pressure when worn, to closely engage a portion of the patient's body. The splint body 12 is also molded to closely engage a portion of the patient's body as it is disposed in a desired position such that the elastomeric body 12 biases such portion of the patient's body to the desired position. This desired position may be a position which promotes proper mending of bones, or healing of tendons or muscle tissue, or it may be the desired at rest position of the patient's body portion to overcome displacement caused by palsy or bone deformity.

The splint 10 can be fashioned to engage various parts of a patient's body, and to totally or partially immobilize such portions of the body of the patient. For example, in FIG. 2 an improved splint for the wrist 23 and hand 24 is illustrated at 10A. Hypothesizing injury to the finger 20, and presuming a desired patient body position in which the finger 20 is at least partially closed, the splint 10A has been molded such that the inner surface 14 conforms to the exterior contours of the lower arm 22 and finger 20 when in such desired position such that the resilient splint body 12 biases the finger 20 to the desired position.

It will be noted that in FIG. 2, the fingers 17–19 and the thumb 21 remain unrestricted. However, should the desired remedial position require, the splint body 12 can be molded to immobilize, or reduce the mobility of, the fingers 17–19, as illustrated in FIG. 3 in the embodiment labelled 10B. It is conceivable that a splint 10 may be molded to at least partially reduce the mobility of the thumb 21, as well. In this regard, it is contemplated that a splint 10 can be pre-molded to provide a preselected maximum area of restricted mobility and later trimmed to engage a lesser patient body area as may be required. For example, the splint of FIG. 3 can be pre-molded to the configuration of 10B and, prior to being secured on the body of the patient, trimmed to the configuration 10A such that the fingers 17–19 are not needlessly restricted. It will be appreciated that the use of a suitable elastomeric fabricating material, such as silicone rubber, permits the splint 10 to be easily trimmed using cutting instruments generally available to a physician in general practice. Such fabrication also permits the shaving of the splint 10 in order to reduce the thickness and enhance the flexibility, which will be appreciated in the progressive states of healing. Further, it will be appreciated that the use of an elastomeric material permits the splint to be worn while the wearer bathes because the material is waterproof.

Figure 4:
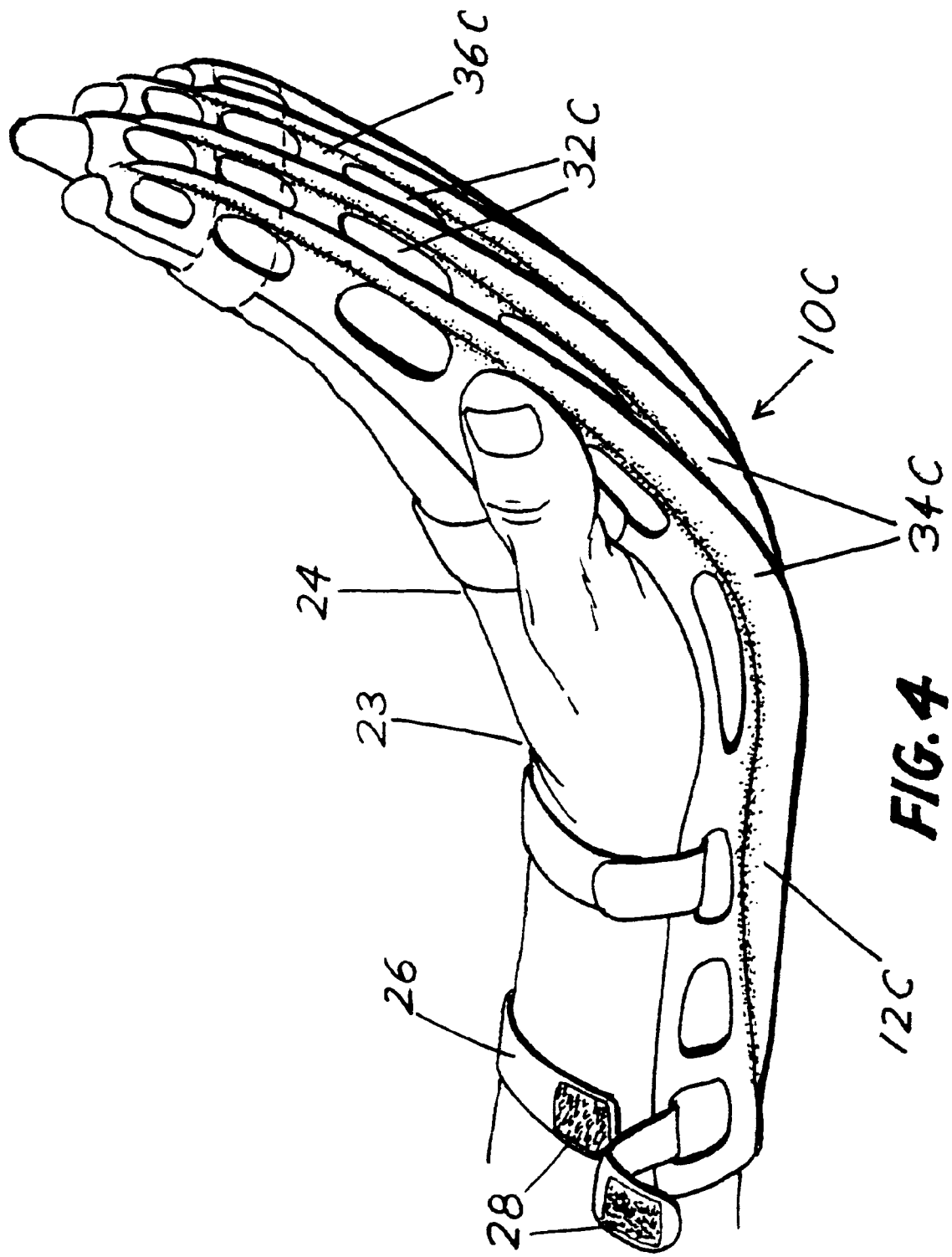
FIG. 4 is a perspective view of an alternate embodiment of an improved splint/therapeutic device of the present invention.

In order to secure the splint 10 to the body of the patient, a suitable securing means is provided. Such means can include adhesive or other suitable tapes, or various releasable straps. However, in the embodiment illustrated in FIG. 2, the splint 10A includes one or more adjustable straps 26 which are received around the associated patient's body part and around the splint 10, and adjustably secured with a hook-and-loop fastener such as the illustrated hook-and-loop type fastener 28, as best illustrated in FIG. 4. It will be appreciated that the straps 26 allow the splint 10 to be quickly and easily secured or removed, and the tightness of the straps 26 can be easily adjusted to provide for a comfortable fit. Of course, the number and placement of the straps 26 will vary depending upon the configuration of the splint 10 and the portion of the patient's body to which it is to be secured, as is reflected in the figures.

Alternatively, the splint body 12 can define strap receiving slots 60 which are molded into the splint body 12. The strap receiving slots 60 are situated on either side of the splint body 12 and receive the straps 26. The straps 26 can be a singular strap which is secured to itself or a set of straps, one end of each being secured to a strap receiving slot 60 and the other end of each being secured one to another. With this configuration the splint body 12 is secured to the body portion, but the straps 26 do not encircle the splint body 12 and the body portion. This configuration may be desirable when providing a splint that supports the neck, for example. Further, it may be desirable to mold gussets 62 into the splint body 12, such as the type shown in FIG. 28. The gussets 62 can receive the straps 26 and provide reinforcement to a high stress area.

The securing means can also comprise patient body encircling portions integrally formed with the splint body 12 if desired. For example, in the embodiments of FIG. 15 the securing means is a molded strap 61. Molded straps 61 are integrally formed with the splint body 12, thereby obviating the need for separate securing means. Of course, this can be accomplished by molding the straps 61 during the initial manufacturing process.

The splint 10 typically defines openings 32 such that the overall weight of the splint 10 is reduced and further to provide for the aeration, temperature control, and moisture control of the body portion to which it is secured. The openings 32 are defined at selected locations which do not carry substantial tensile or compressive loads placed upon the splint 10, the loads normally exerted at those locations being distributed to adjacent portions of the splint 10.

In FIG. 4, the splint 10C is molded to bias the hand 24, and the fingers 17–20 and thumb 21 to a fully opened position. The splint 10C will allow for the relaxation of the extensor tendons after surgical repair of the same. When the extensor tendons begin to heal, exercise may be gradually increased. Early mobilization, as has been discussed, will promote more rapid healing.

Figure 5:
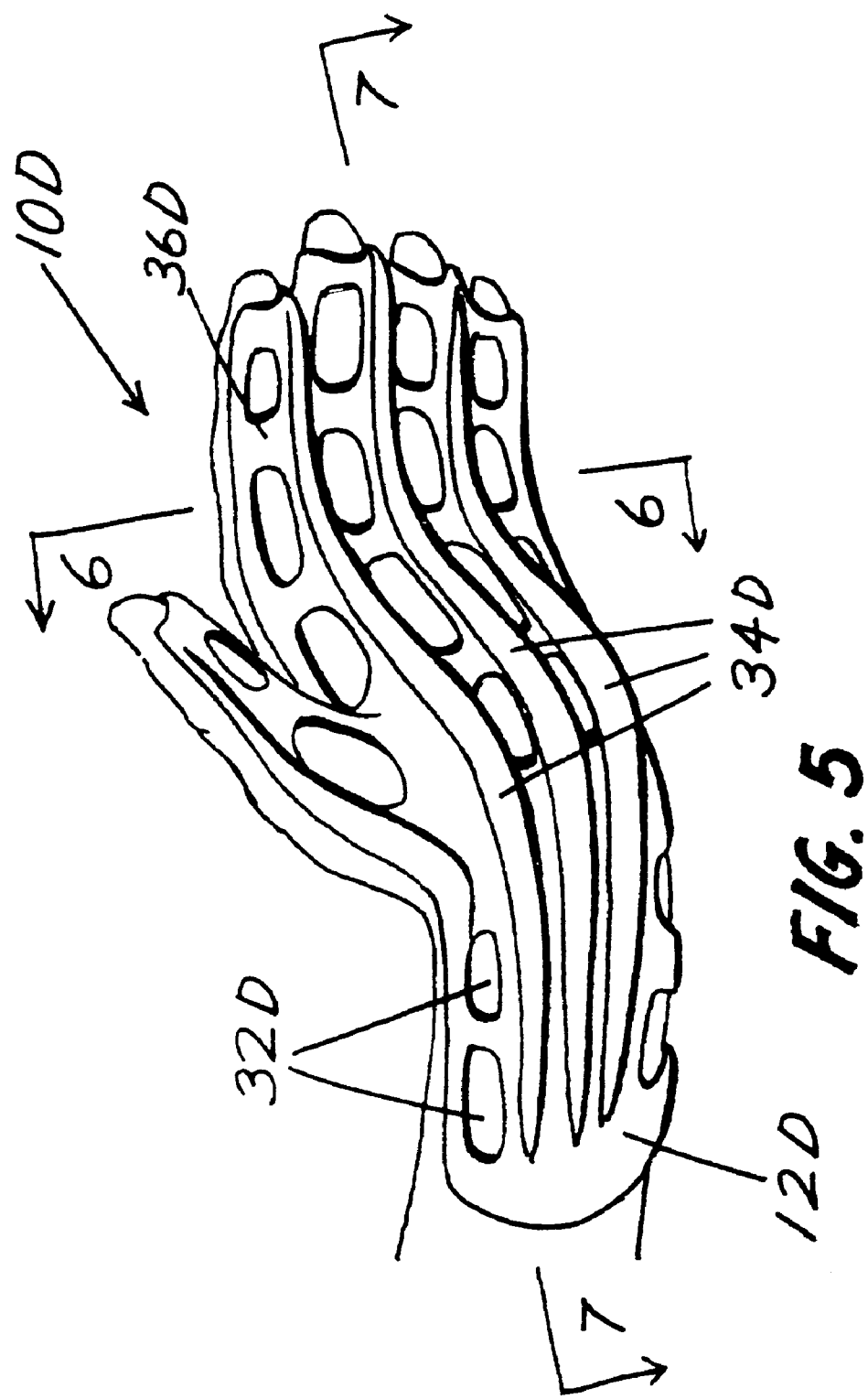
FIG. 5 is a perspective view of an alternate embodiment of an improved splint/therapeutic device of the present invention.
Figure 6:
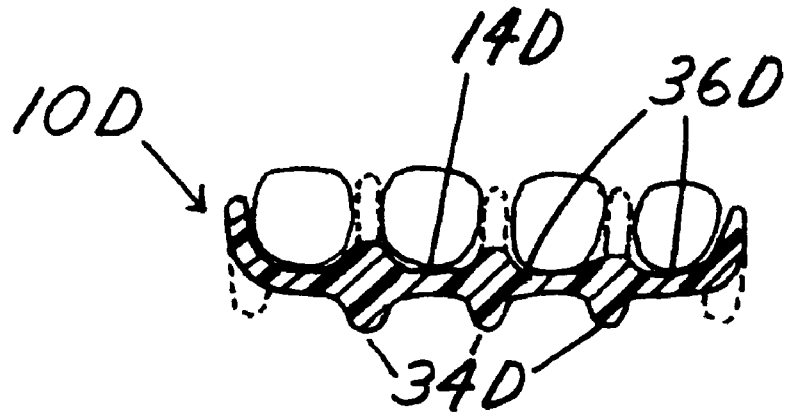
FIG. 6 is an end view, in section, of the alternate embodiment of the improved splint/therapeutic device of the present invention as illustrated in FIG. 5.
Figure 7:
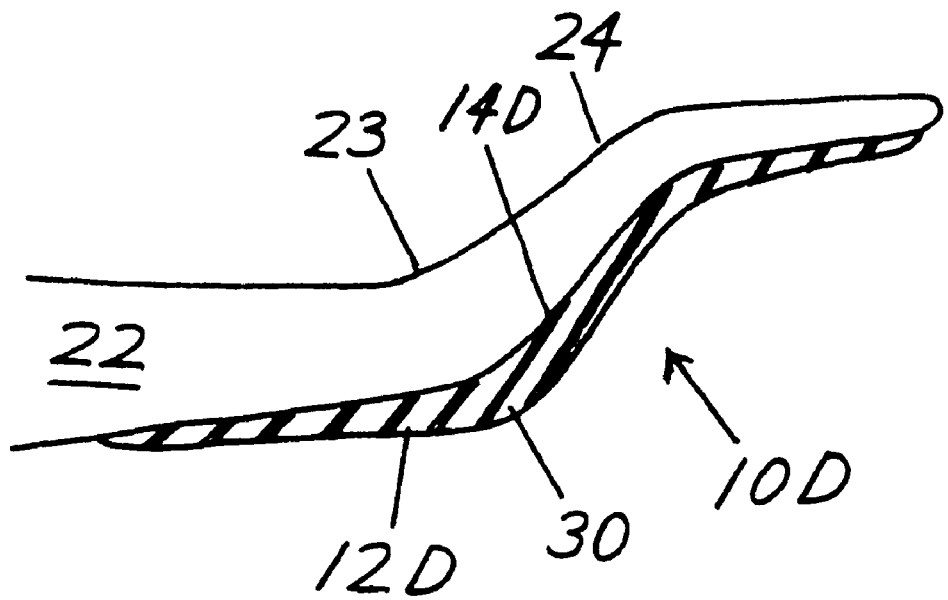
FIG. 7 is a side view, in section, of the alternate embodiment of the improved splint/therapeutic device of the present invention as illustrated in FIG. 5.

FIG. 5 illustrates a similar embodiment to that of FIG. 4. However, the splint 10D biases the wrist in a position further back than the splint 10C. Due to the nature of the preferred material for construction, the splint 10D may be attained by heating a splint 10C until malleable, and then by molding the splint 10C to the selected position. FIG. 5 is illustrative of the numerous configurations in which the present splint 10 may disposed. FIG. 6 illustrates a cross-sectional view of the splint 10D wherein a plurality of ribs 34 are defined which are greater in thickness than the lateral portions 36 of the splint body 14. The ribs 34 provide for the at least partial immobilization of the fingers 17–20 and thumb 21, while the thinner lateral portions 36 maintain the relative positions of the ribs 34, the reduced thickness aiding in minimizing the weight of the splint 10D.

The amount of resistance to movement imparted by the splint 10 is preselectively controlled by varying the thickness of the splint body 12. It will be understood by those skilled in the art that the force necessary to deform the elastomeric material of the body 12, such material typically being of substantially uniform density, increases with the thickness of such material. Therefore, the splint body 12 is provided with one or more portions or areas having increased thicknesses to produce a greater resistance to movement of the patient's body proximate that area. This is best illustrated in FIG. 6 where the body 12 of the splint 10 is provided with a portion of increased thickness 30 which engages the patient's body beneath the wrist 23 thereby increasing the resistance to motion at the wrist 23 relative to the other areas of engagement.

Of course, if greater wrist mobility is desired, the thickness of the splint body 12 at the portion 30 can be decreased. This can be accomplished by pre-molding the splint 10D with a thinner portion 30 or by cutting away the fabricating material to produce a thinner portion 30. Thus, with respect to the degree of mobility of various other body portions can be controlled by providing the body 12 with the appropriate thickness at the portion of the splint body 12 which engages the body portion.

It may be desirable to reduce or increase the elasticity of the splint without substantially reducing or increasing the thickness of the splint. For example, to reduce the elasticity of the splint, elastomeric stiffeners, such as the type shown in FIG. 27, may be molded into the splint body to provide a less elastic splint.

Figure 42:
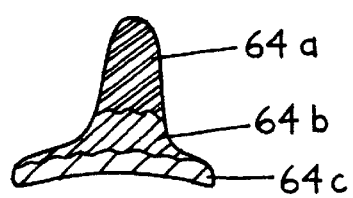
FIG. 42 is a cross sectional view of a portion of a splint body with regions of varying moduli of elasticity.

Of course, other materials can be used which increase or decrease the elasticity. It is conceivable to utilize a material in which the modulus of elasticity can be varied by treatment of sections of the material. For instance, some materials, such as a variety of polymers, when irradiated, undergo a change in the modulus of elasticity. The thickness and extent of the regions of differing moduli of elasticity can be controlled such that a desired flexibility is attained. Further, it will be noted that different materials with varying moduli of elasticity can be molded together to produce the desired flexibility. An example of a cross section of a material with a varying modulus of elasticity is shown in FIG. 42. In this particular example, there are three different regions 64a, 64b, 64c with different moduli of elasticity. It will be noted that the number of regions with differing moduli of elasticity can vary.

It will be recognized by those skilled in the art that the resistance to patient mobility provided by the splint apparatus 10 allows the splint 10 to be utilized to resistively exercise muscles and tendons. Moreover, by selectively varying the flexibility of the resilient body 12, the resistive exercise provided can be selectively apportioned to the various patient body portions to which the splint is applied. With respect to the splint 10D of FIG. 5, for example, damage to the wrist 32 may call for the thickness of the ribs to be substantial in order to immobilize the wrist 32, but it may be desirable to provide resistive exercise to the fingers 17–20 and the thumb 21 to avoid atrophy of the muscle tissue. Thus, the ribs can be molded to define a lesser thickness proximate the fingers 17–20 and thumb 21 so as to allow movement of the fingers 17–20 and thumb 21 against the bias of the body 12, thereby exercising the operatively associated muscles. Further, as the healing process continues, it may be desirable to provide some mobility to the wrist 23 of the patient, and commence rehabilitation of the operatively associated muscles and tendons. This can be accomplished by reducing the thickness of the ribs 34 proximate the wrist 23. Alternatively, a material with varying moduli of elasticity can be utilized wherein the outer layer is less flexible and the inner layer is more flexible. With this configuration, the outer layer can be shaved away resulting in a more flexible splint.

As noted above, the splint 10 can be applied to various parts of a patient's body and further examples of various applications are illustrated in FIGS. 8–26, FIGS. 29–41 and FIGS. 43–46. FIGS. 8–18 are primarily used for restraining the fingers 17–20 and the thumb 21. The remaining Figures illustrate the splint 10 applied to other parts of a patient's body. It is noted that it may be desirable to incorporate some type padding around the edges of the splint body such that the splint body does not pull the patient's skin.

FIG. 8 illustrates a straight splint 10E which may be used to retain a finger as shown. In the preferred embodiment shown, ribs 34 are integrally formed with lateral portions 36 encircling the finger, with openings 32 defined therebetween for the clearance of the knuckles. As shown in the cross-sectional views of FIGS. 9–11, the thickness of the ribs 34 may be varied from one end to another. The embodiment shown is thicker toward the palm, thereby allowing for greater flexibility at the end of the finger as opposed to the flexibility at the base. In FIG. 12, an L-shaped splint 10F is illustrated for reducing the mobility of a finger.

FIG. 13 illustrates a U-shaped splint 10G for biasing the thumb and forefinger to selected positions. Such an embodiment may be desired in cases such as that illustrated in FIG. 14, which depicts the position of a hand 24 crippled with arthritis, palsy, or other similar disablement which causes a spasmed closed hand.

Figure 15:
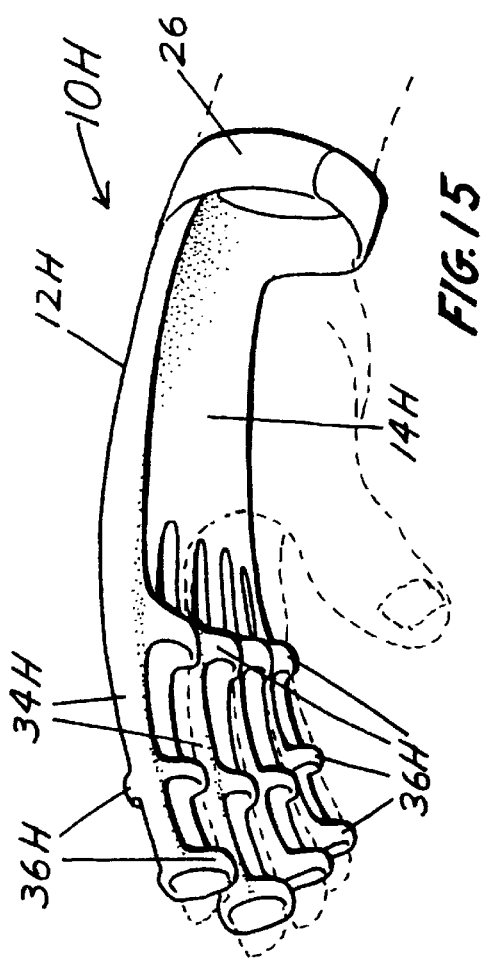
FIG. 15 is a perspective view of an alternate embodiment of an improved splint/therapeutic device of the present invention.
Figure 16:
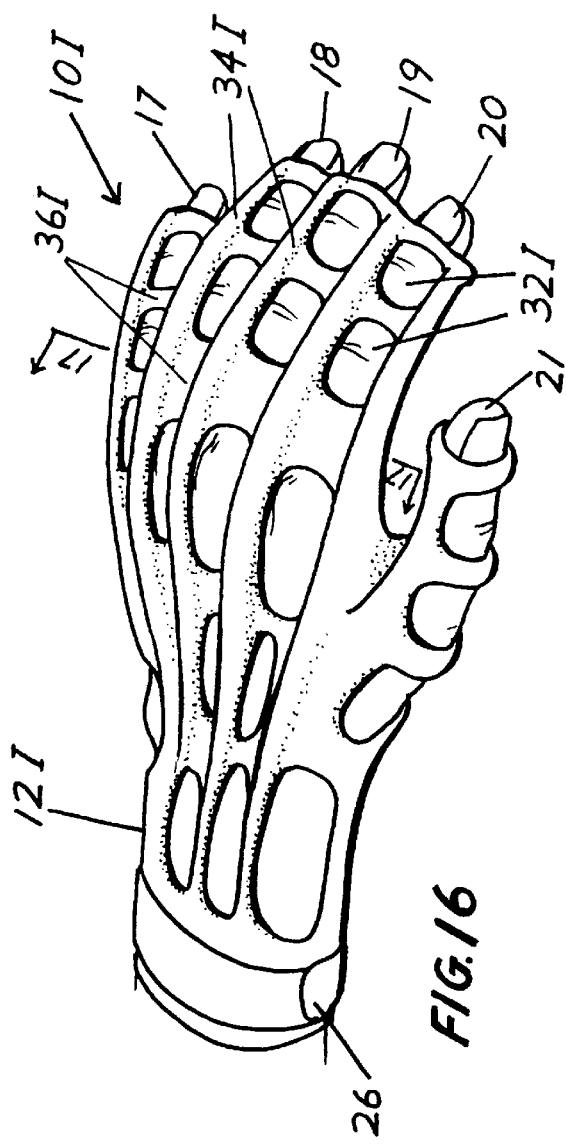
FIG. 16 is a perspective view of an alternate embodiment of an improved splint/therapeutic device of the present invention.

The splints 10H, 10I and 10J of FIGS. 15, 16 and 18, respectively, depict splints for restricting the mobility of a plurality of the fingers 17–20 and the thumb 21. The splint 10H may be used to at least partially immobilize the fingers 17–20 independently one from the other. The finger retaining portions are similar to the splint 10E described above and depicted in FIG. 8.

The splint 10I as shown may be used to at least partially immobilize the fingers equally. FIG. 17 illustrates a cross-sectional view of the splint 10I wherein ribs of varying thicknesses are incorporated. The ribs may be selectively cut along the centerlines 35 shown in order to allow for the independent mobilization of selected fingers.

The splint 10J shown in FIG. 18 is similar to the splint 10I shown in FIG. 16. However, the splint 10J as shown will allow for the complete mobility of the finger 20 and the thumb 21. This embodiment may be achieved by trimming the respective portions of the splint 100 which would otherwise at least partially immobilize the finger 20 and the thumb 21.

Figure 19:
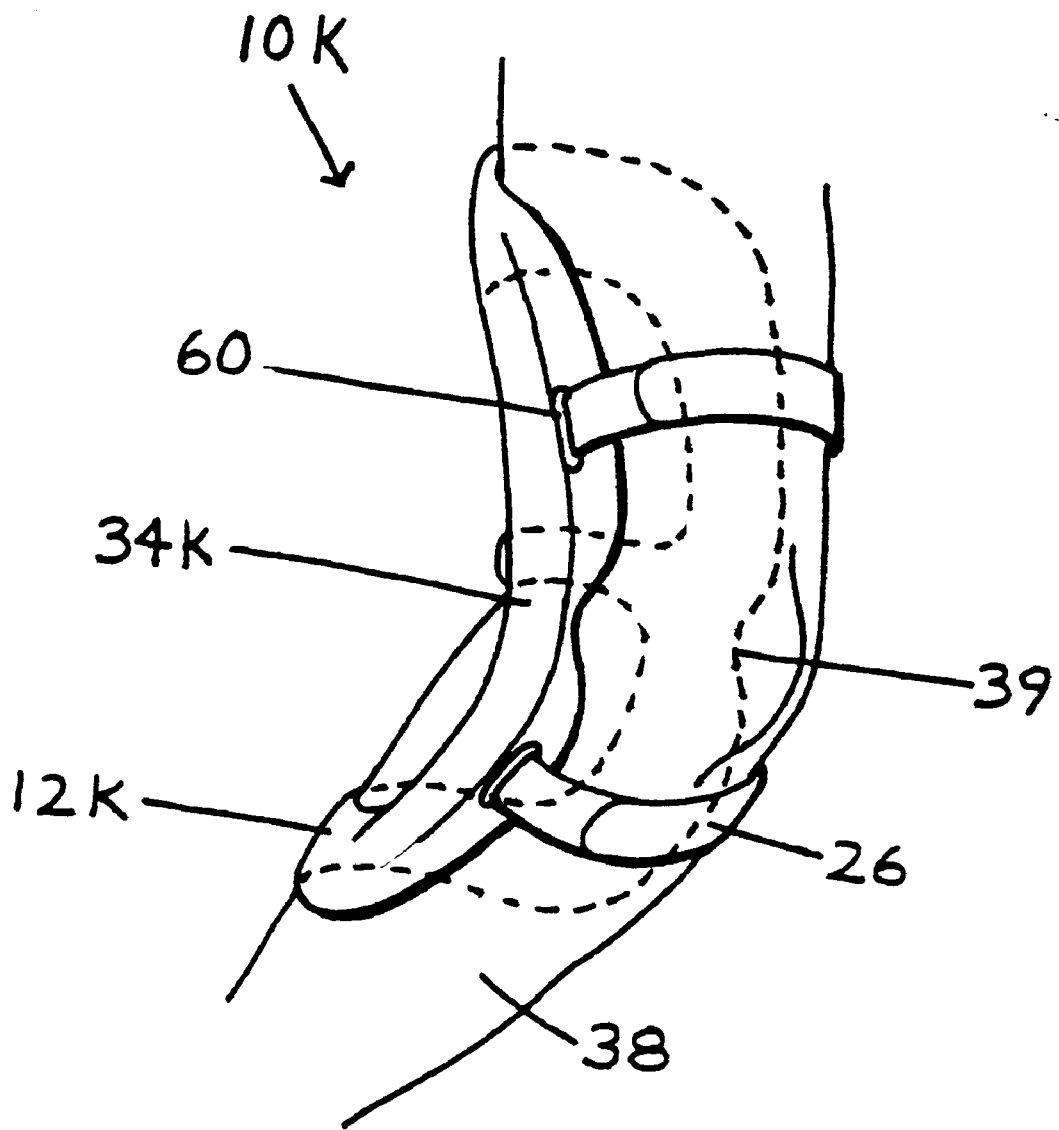
FIG. 19 is a perspective view of an alternate embodiment of an improved splint/therapeutic device of the present invention.
Figure 20:
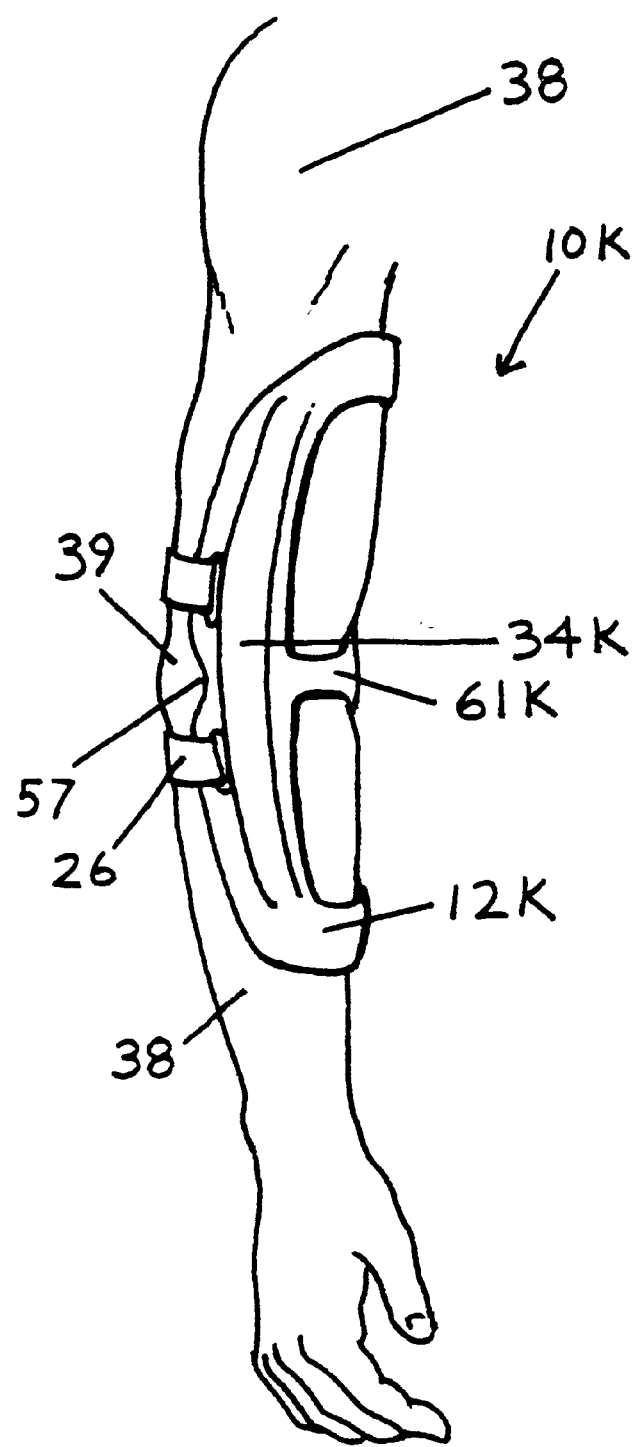
FIG. 20 is a perspective view of the alternate embodiment of the improved splint/therapeutic device of FIG. 19.

FIGS. 19 and 20 illustrate a splint 10K for restricting the mobility of an elbow 39. Such an embodiment may be desired for training or therapy, wherein the elbow 39 is biased in an extended position but can be flexed and bent. The splint body 12K is configured to fit the arm 38, as shown in FIG. 19. The straps 26 are secured to each other on either side of the elbow 39 and a molded strap 61 positioned to fit at the inner arm opposite the elbow 39. The ribs 34K run the length of the splint body 12K along the arm 38 such that the arm 38 is biased in the preselected position. It will be noted that the splint 10K can be molded to bias the arm 38 in a bent position or a straightened position. It may be desirable to mold an indent 57 into the splint body 12K such that the splint 10K is prone to bending at a preselected location. It is conceivable that the splint 10K can be used to support the knee, wherein the splint 10K is configured to fit the around the leg at the knee and the straps 26 are secured around the knee.

Figure 21:
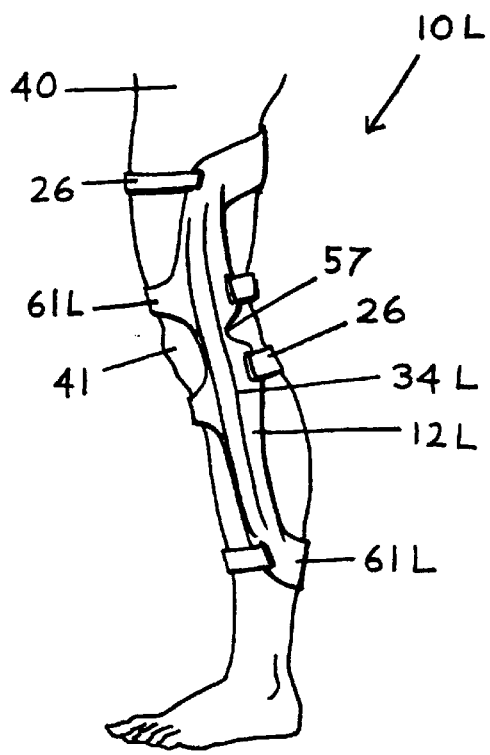
FIG. 21 is a perspective view of an alternate embodiment of an improved splint/therapeutic device of the present invention.
Figure 22:
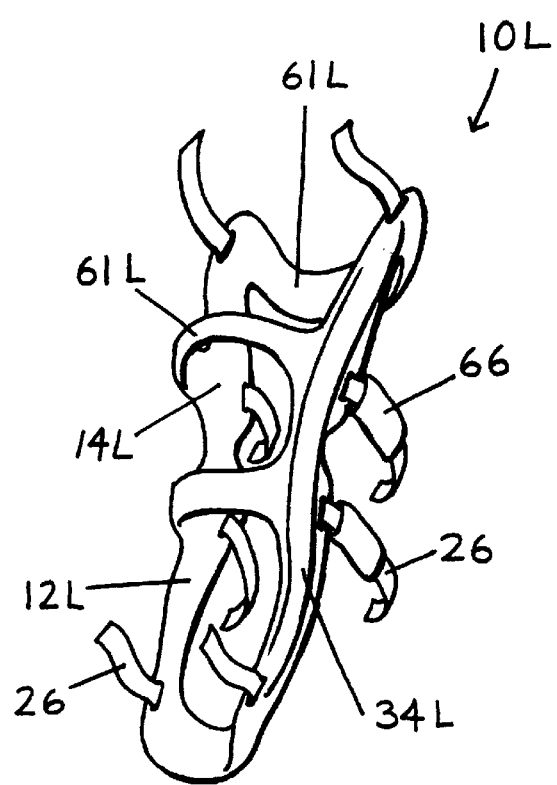
FIG. 22 is a perspective view of the alternate embodiment of the improved splint/therapeutic device of FIG. 21.

FIGS. 21 and 22 illustrate a splint 10L for restricting the movement of the knee 41. The splint 10L provides ribs 34L which run down the length of the splint body 12L on either side of the knee 41 and provide support to the knee 41. The splint body 12L defines molded straps 61. One secures around the leg 40 at the upper thigh, two secure around the knee 41, one above and one below, and a fourth secures around the leg 40 at the lower calf. Such an embodiment may be desired in a case where the knee 41 is injured and support around the knee 41 is necessary. As shown clearly in FIG. 22, the straps 26, which secure around the back of the knee 41, are equipped with comfort pads 66, such that the straps 26 do not cut into the leg 40 of the patient. Also note that the splint body 12L defines an indent 57 such that the splint body 12L is prone to bend at a preselected location.

Figure 24:
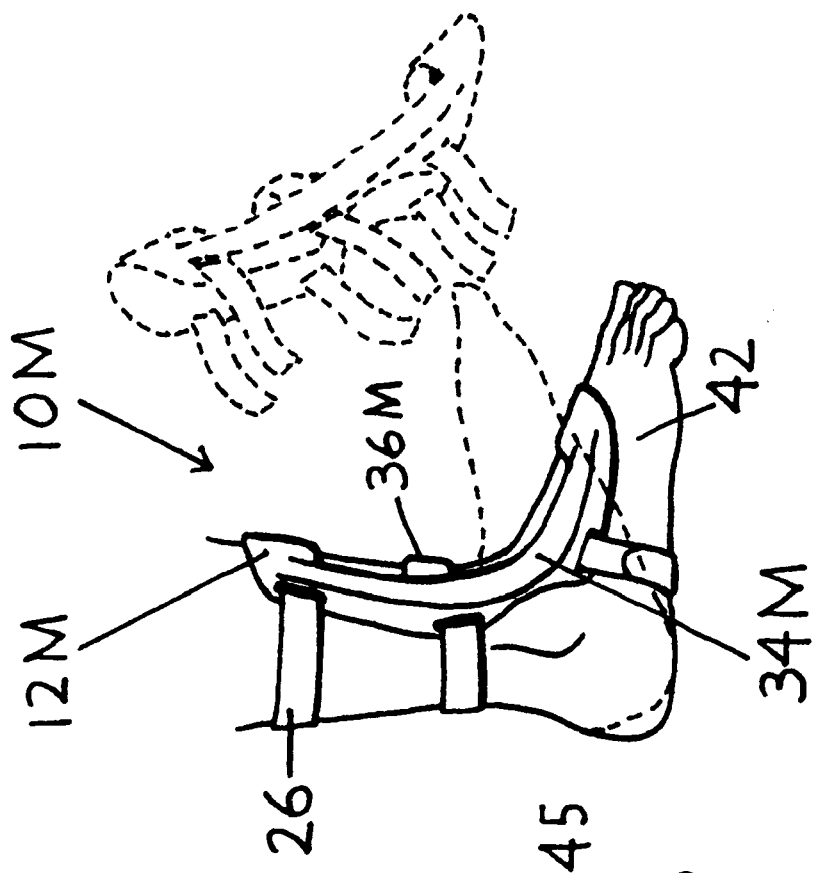
FIG. 24 is a perspective view of an alternate embodiment of an improved splint/therapeutic device of the present invention.
Figure 23:
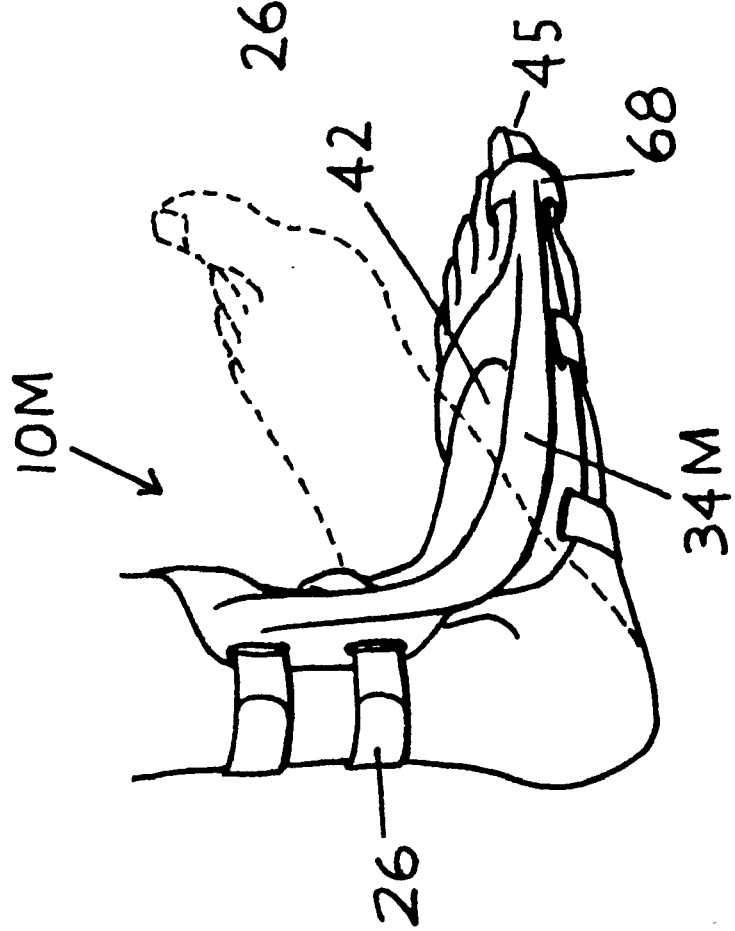
FIG. 23 is a perspective view of a human foot which is spasmed upward.

FIGS. 23 and 24 depict a splint 10M which can be utilized in correcting a spastic foot 42 which pulls upward, as shown in FIG. 23. The splint body 12M is configured to fit the top portion of a patient's foot 42 and force the foot 42 downward. Toe extensions 68 can be incorporated into the construction of the splint 10M to support a spastic toe 45. Preferably, the toe extensions 68 extend from the top or side portion of the splint 10M, as shown in FIG. 23, and force the spastic toe 45 downward. FIG. 24 shows the splint 10M, as it appears before it is strapped to the spastic foot 42, and the spastic foot 42, in phantom. The splint 10M, once secured to the foot 42, forces the foot 42 downward into a normal position. The ribs 34M run the length of the splint body 12M and serve to force the foot 42 downward. It will be noted that the elasticity of the splint 100 can be increased or decreased depending upon the severity of the case.

FIGS. 25 and 26 illustrate a splint 10N which is used to support a foot 42 which hangs or spasms downward, as depicted in phantom in FIG. 25. The splint body 12N is configured to receive the bottom of the foot 42 and the back of the ankle 43. The splint 10N is molded to force the foot 42 up. Of course, the modulus of elasticity molded into the splint 10N can be altered depending upon the severity of the case.

The splints 10L, 10M, 10N permit the patient to walk while wearing the splint.

Figure 29:
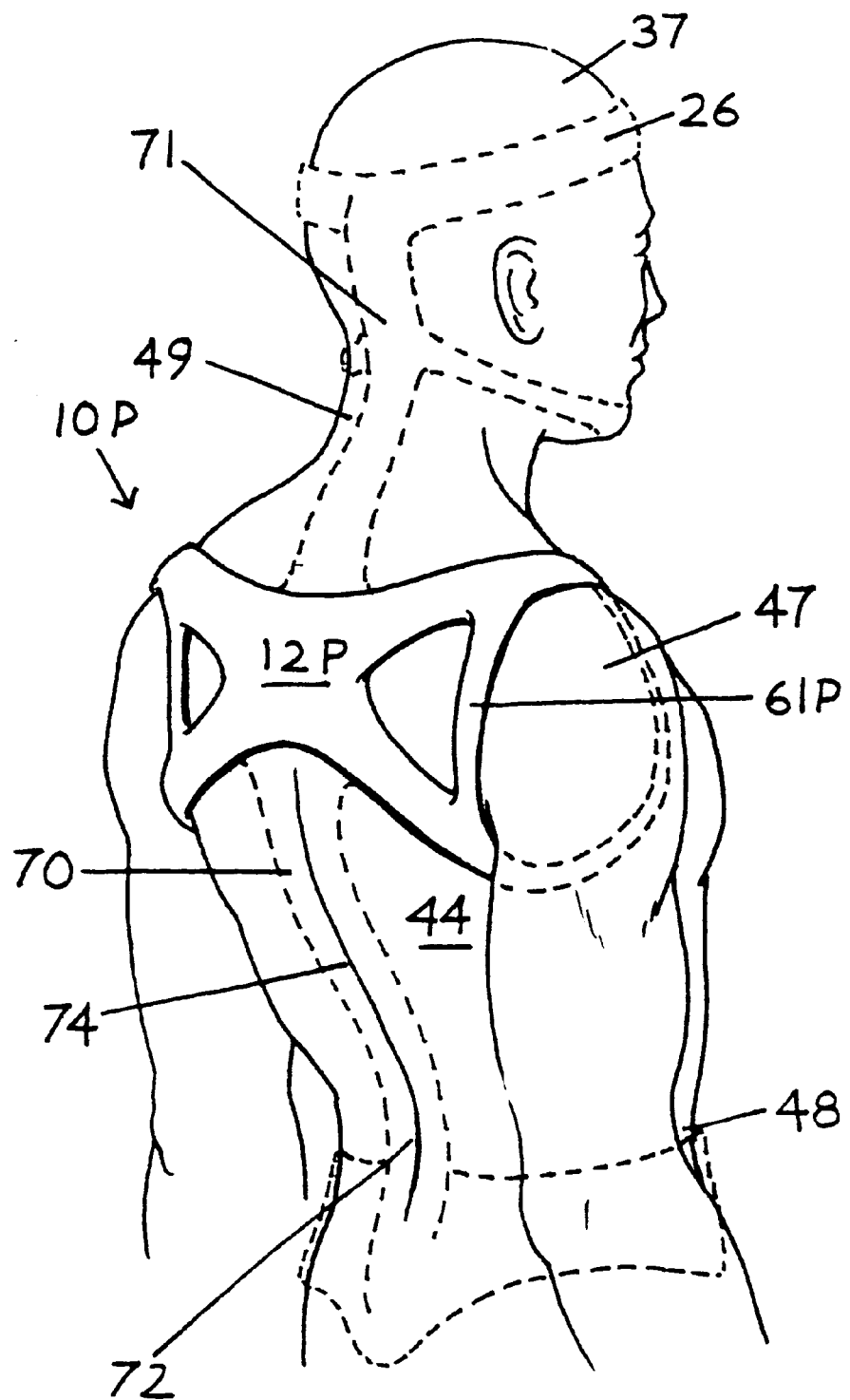
FIG. 29 is a perspective view of an alternate embodiment of an improved splint/therapeutic device of the present invention.
Figure 30:
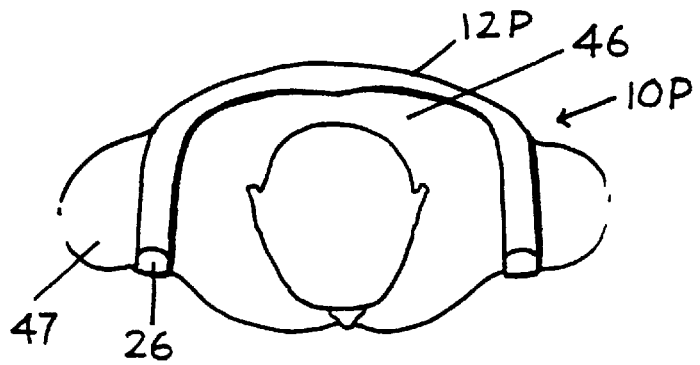
FIG. 30 is a top view of the improved splint/therapeutic device of FIG. 29.
Figure 31:
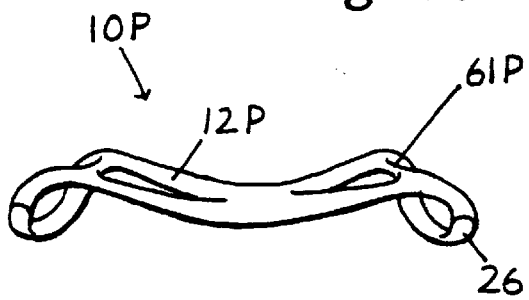
FIG. 31 is a top view of the improved splint/therapeutic device of FIG. 29.

FIGS. 29, 30, and 31 show a splint 10P for use on a human torso 44. Such an embodiment may be used to improve or support the posture. The splint 10P supports the upper back 46. The splint body 12P is carried on the upper back 46 by straps 26 secured around the shoulders 47. As indicated previously, the straps 26 are adjustable. FIG. 31 illustrates a top perspective view of the splint 10P. The splint lop is molded to receive the upper back 46 and the shoulders 47 as shown in FIG. 30. The splint lop defines ribs 34P which cooperate with molded straps or lateral portion 61 and adjustable straps 26 to pull the shoulders 47 back and push the upper back 46 forward in a manner such that the upper back 46 is biased in an erect posture position. The molded strap 61 is configured to fit behind each shoulder 47, as shown in FIG. 29, such that the splint 10P does not slip.

Figure 32:
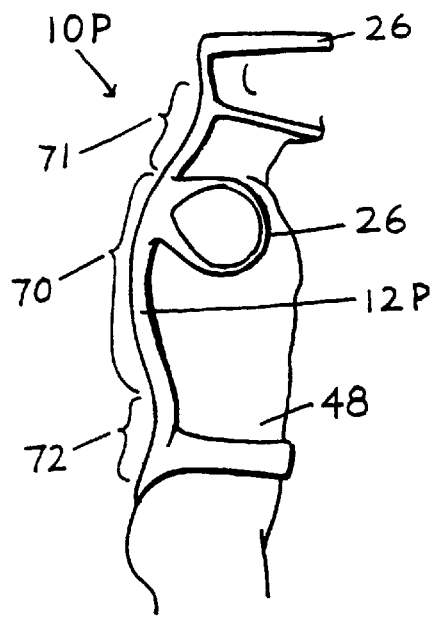
FIG. 32 is a side view of an alternate embodiment of the improved splint/therapeutic device of FIG. 29.

An alternate embodiment of the splint 10P' is shown in phantom in FIG. 29 and a side view is shown in FIG. 32. The splint 10P' includes thoracic 70, cervical 71 and lumbar 72 portions added to the splint 10P, for a more serious posture problem. As shown most clearly in FIG. 32, the lumbar portion 72 is secured around the waist 48 of the patient and the cervical portion 71 is secured around the chin 49 and the head 37 of the patient. The splint 10P' is intended to align the entire spinal column 74. The thoracic portion 70 defines a rib 34P' which is configured to receive the spinal column 74 and force it into a correct position. The cervical portion 71 pulls the head 37 up and holds it straight.

Of course, it is conceivable that the splint 10P' can include only the thoracic and lumbar portions 70, 72, such that the upper back 46 and the remainder of the torso 44 are supported. Also, it is conceivable that the splint 10P' can include only the cervical portion 71 wherein the upper back 46, the neck 49 and the head 37 are supported. Again the flexibility of the splint 10P' can be altered depending upon the condition to be corrected and the severity of the condition.

Figures 33, 34, 35:
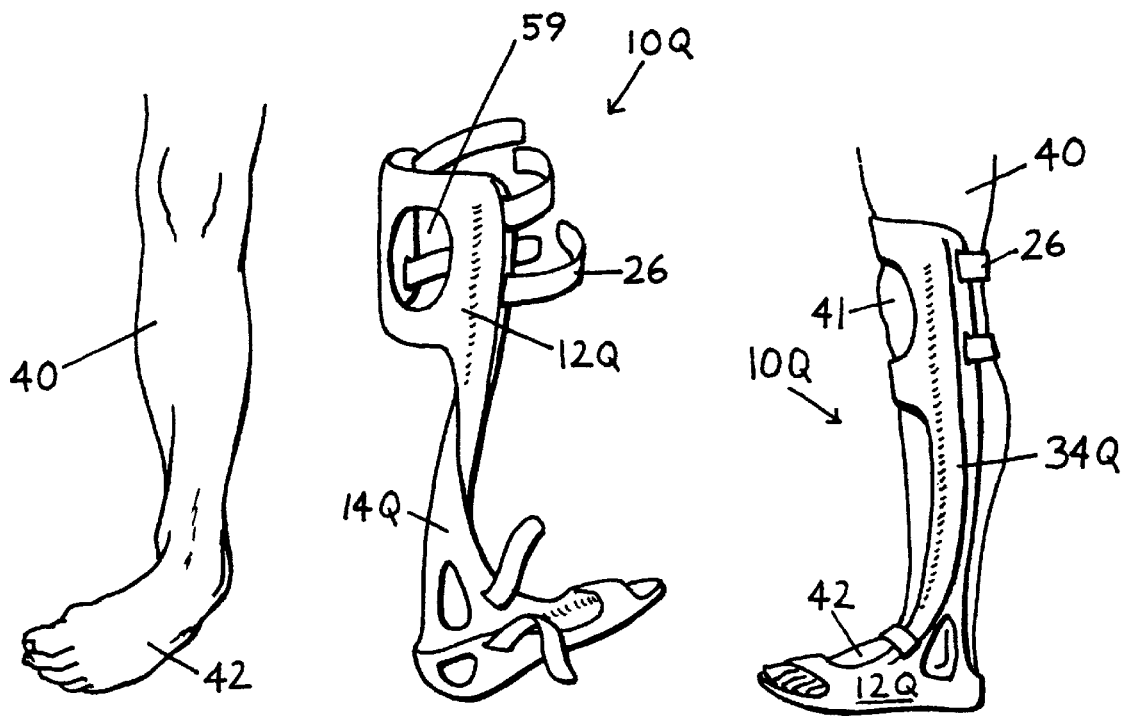
FIG. 33 is a perspective view of a human foot deformed with club foot.
FIG. 34 is a perspective view of an alternate embodiment of an improved splint/therapeutic device of the present invention.
FIG. 35 is a perspective view of the alternate embodiment of the improved splint/therapeutic device of FIG. 34.

FIG. 34 illustrates a splint 10Q which supports a human foot 42 suffering from the condition club foot, which is depicted in FIG. 33. The splint body 12Q is molded to have a twist in the leg segment and a lift in the foot support. The rib 34Q runs down the length of the splint body 12Q. When the foot 42 is placed in the splint 10Q the foot 42 is pulled around and up such that the foot 42 is properly aligned with the leg 40, as shown in FIG. 35. The splint body 12Q defines an opening 59 which receives the knee 41 of the patient such that the splint 10Q does not twist and fail to align the foot 42 properly. With a severe case, it may be desirable to mold a minimal degree of flexibility into the splint 10Q. With minimized flexibility, it may be necessary to configure the splint 10Q to extend up the leg 40 and secure around the waist of the patient. Further, it is not uncommon for both feet 42 to suffer from club foot. In which case, the splint 10Q can be of a unitary configuration to correctly align both feet 42 and molded such that the splint 10Q is secured around the waist.

Figures 36, 37:
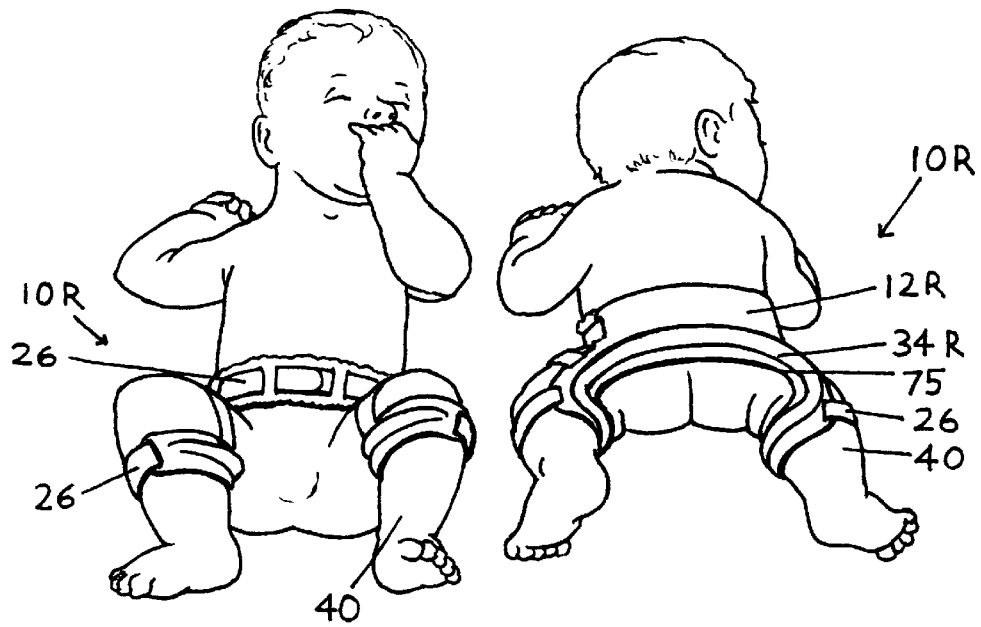
FIG. 36 is a front view of an alternate embodiment of an improved splint/therapeutic device of the present invention.
FIG. 37 is a rear view of the improved splint/therapeutic device of FIG. 36.

FIGS. 36 and 37 illustrate a splint 10R for the hip 75. The splint 10R shown in the Figures would be appropriate for an infant which suffers from congenital dislocation of the hip 75. The splint 10R defines ribs 34R which are configured to pull the legs 40 up such that the ball and socket of the hips 75 are aligned and grow properly. A top portion of the splint 10R is secured around the waist 48 and the lower portion is secured around each leg 40. The splint 10R is configured to provide some flexibility such that the infant can lie on its stomach, but is rigid to maintain the ball of each leg 40 in the socket of the hips 75 in a position to promote proper growth.

The splint depicted in the FIGS. 36 and 37 overcomes several of the problems of the prior art. The prior art is a harness termed the "Pavlik harness". It is a complicated device with a number of securing straps which fit around numerous portions of the infant's body to properly maintain the hips in the selected position. The splint 10R of the present invention is a simple unitary construction with securing straps that are easily secured.

Figure 38:
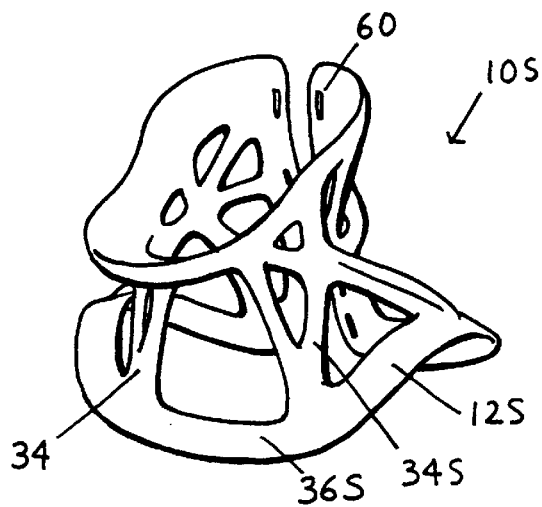
FIG. 38 is a perspective view of an alternate embodiment of an improved splint/therapeutic device of the present invention.
Figure 39:
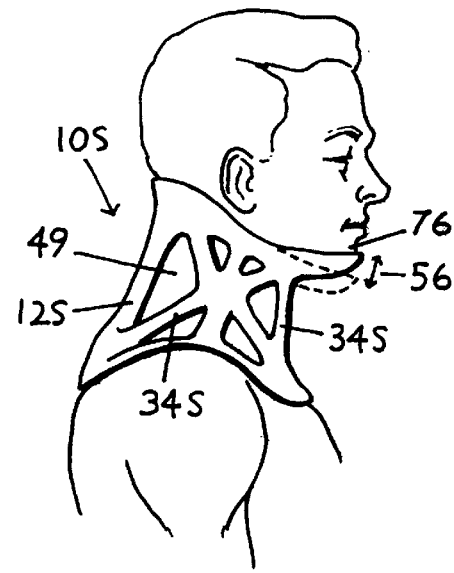
FIG. 39 is a side view of the alternate embodiment of the improved splint/therapeutic device of FIG. 38.
Figure 40:
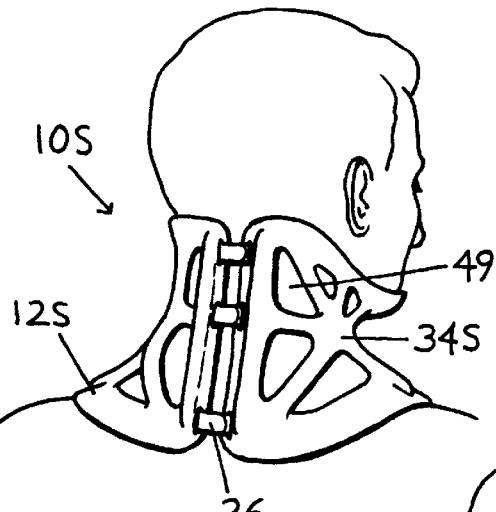
FIG. 40 is a rear view of the alternate embodiment of the improved splint/therapeutic device of FIG. 38.

FIGS. 38, 39 and 40 illustrate a splint 10S for supporting and restricting the mobility of the neck 49. FIG. 39 shows a side view of the splint 10S and depicts the limited motion provided to the chin 76, indicated in phantom and by the arrow 56. The limited motion of the chin 76 is permitted by molding the splint 10S such that a higher degree of flexibility is molded into the ribs 34S supporting the chin 76. FIG. 40 illustrates a rear view of the splint 10S wherein the securing straps 26 are shown. It is preferable that strap slots 60 are molded into the rear portion of the splint 10S to receive the adjustable securing straps 26, shown most clearly in FIG. 38. The ribs 34S are interconnected in a manner such that a plurality of openings 32 are defined for ventilation.

Figure 41:
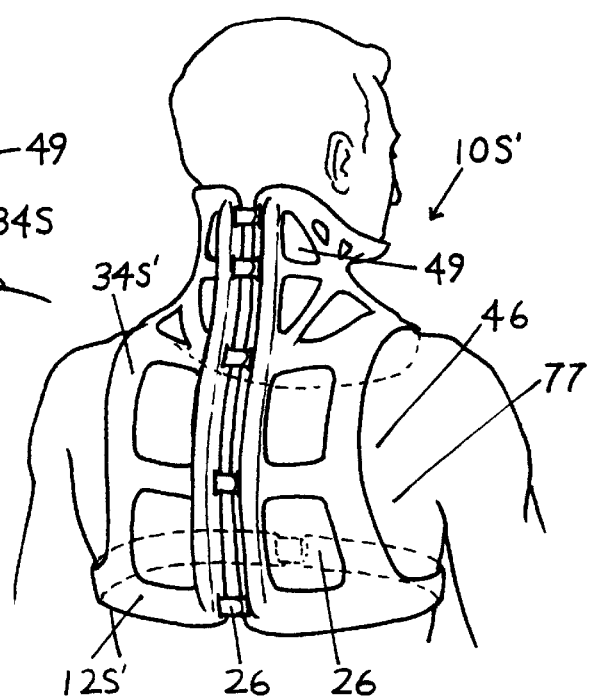
FIG. 41 is a perspective view of an alternate embodiment of an improved splint/therapeutic device of the present invention.

FIG. 41 illustrates an alternate embodiment of the neck splint 10S of FIG. 38. The splint 10S' which supports the upper back 46 as well as supporting the neck 49. The splint 10S' defines ribs 34S' which support the upper back. Further, the splint 10S' defines additional strap slots 60 in the rear of the splint 10S' and an adjustable strap 26 that secures around the chest 77 of the patient such that the splint 10S' securely supports the upper back 46.

In an alternate embodiment, the splint 10 includes three restraints 80 around a joint, two on one side of the splint and one on the opposing side of the splint proximate the joint. The restraints 80, each of which is defined by a molded strap 61 or an adjustable strap 26, are located to maintain the body part in a biased position. A splint 10 with three restraints 80 as described is more easily and less expensively manufactured because full ring structures do not have to be considered in the molding process. FIGS. 43–48 illustrate splints which define three restraints 80 located in the manner described.

FIGS. 43 and 44 illustrate a splint 10T for a finger 20 including three restraints 80 defined by three molded straps 61. Two of the molded straps 61 or lateral portions are positioned at opposing ends of the splint 10T and support the under side of the finger 20. The third molded strap 61 is positioned proximate the joint and supported by the upper side of the finger 20. The splint 10T can be molded to be stiffer by changing the elastomeric formula. Further, the splint 10T can be molded in a flexed position.

FIGS. 45–52 illustrate splints 10V, 10W, 10X, 10Y for supporting the wrist 23 of a patient. The splints illustrated in these Figures are utilized to partially or substantially immobilize the wrist 23 to ease or prevent injury to the wrist 23.

FIGS. 45 and 46 illustrate a splint 10V which can be utilized to prevent or alleviate carpal tunnel syndrome. The splint body 12V defines ribs 34V interconnected via lateral portions 36V and an adjustable strap 26 to support the wrist 23. Specifically, a lateral portion 36V supports the under side of the hand 24, another lateral portion 36V supports the upper side of the arm proximate the wrist, and an adjustable strap supports the under side of the lower arm 22. In the preferred embodiment, the lateral portion 36V proximate the wrist 23 is padded (not shown). The splint 10V defines ribs 34V which are stiff enough to stabilize the wrist 23 during work at a keyboard, etc. yet flexible enough for comfort, allowing full time wearing even during sleep or bathing. The splint 10V is open at the under side of wrist 23 to keep pressure off the annular ligament or the carpal area 88. It will be noted that the adjustable strap 26 can be configured to wrap around the splint body 10V and the arm 22.

FIGS. 47 and 48 illustrate a splint low similar to that of FIGS. 45 and 46 wherein the splint body 12W defines ribs 34W which are connected via lateral portions 36W. The splint 10W defines a molded strap 61 for receiving the underside of the arm 22. The molded strap 61 includes a strap length adjustor 78. In the preferred embodiment, molded strap 61 includes a first molded strap 84 and a second molded strap 86 which are secured together by mating at least one of a plurality of openings 80 defined by the first molded strap 84 and at least one of a plurality of nodules 82 defined by the second molded strap 86. The length of the strap 61 is adjustable by increasing or decreasing the number of nodules 82 and openings 81 mated. It will be noted that any means for adjusting the length of the molded strap 61 would be suitable. With a molded strap 61, the entire splint 10W is fabricated from the resilient, water proof material thereby providing a splint which is easily cleaned. Further, the strap length adjustor 78 permits the splint 10W to be adjustable to fit a number of patients with varying wrist and arm sizes. This type of splint 10W is useful in food processing, for example, where the splint 10W can be worn while processing food, removed, cleaned and reused.

FIGS. 49 and 50 illustrate a splint 10X wherein the splint body 12X defines a network of ribs 34X for supporting more advanced cases of carpal tunnel syndrome or other repetitive motion disorders. The splint 10X illustrated defines a molded strap 61 with a length adjustor 78, as described above. It will be noted that although a molded strap 61 for supporting the under side of the lower arm 22 is illustrated, an adjustable strap 26, as shown in FIG. 4, is also suitable. The construction of the splint to include adjustable straps 26 or molded straps 61 is dictated by the end use of the particular splint.

FIGS. 51 and 52 illustrate a splint 10Y wherein the splint body 12Y defines ribs 34Y for supporting under the wrist 23 of the patient. The network of ribs 34Y leaves the carpal tunnel region 88 open such that undue pressure is not placed on the region 88. This splint 10Y is useful for a more serious case of carpal tunnel syndrome or a sprained wrist.

In an alternate embodiment (not shown), the splint 10X of FIGS. 49 and 50 and the splint 10Y of FIGS. 51 and 52 may be used together to support the wrist 23 of a patient.

It will be noted that because of the attributes of the resilient material used to manufacture the splints of the present invention, the splints can be worn and used in a variety of activities. For example, the splints can be worn while bathing or during hydrotherapy because the material is waterproof. Further, for resilient or elastomeric materials which are not alterable by irradiation, the splints can be worn while x-rays are taken because the material does not interfere with x-rays. Moreover, as discussed above, the resilient and elastomeric materials can be heated to reform or remold the splint. Also, the splints are constructed to provide airiness such that the skin does not become irritated and can be scratched.

It is envisioned that other embodiments may be developed beyond the embodiments discussed heretofore. In these embodiments, the same subject matter herein disclosed may be adapted to achieve similar results for other body portions. It is also envisioned that the embodiments can be adapted to be used on animals. It is noted that some type of deterrent against chewing the splint may be necessary when a splint is used on an animal. One possible deterrent may be impregnating the splint material with a foul tasting substance.

In light of the above, it will be recognized that the present invention provides an improved splint with great advantages over the prior art. Unlike conventional splints, the splint 10 allows the physician to preselect the extent to which the patient's body is immobilized, and a splint 10 can impart greater immobility to certain portions of the patient's body which it contacts than others. The ability to trim or otherwise control the flexibility of the splint 10 to fit the particular injury or application makes it more versatile than conventional splints and obviates the need for various different splint configurations for the same general body portion. This ability to trim or adjust the flexibility of the splint 10 also allows openings to be cut in the body 12 of the splint to provide access to lacerations without compromising the immobilization of the patient's body portion. The splint 10 can be used to immobilize, or partially immobilize, bone fractures, or damaged tendons or muscles, and can also be used as to resistively exercise muscles and/or tendons to overcome or prevent atrophy of such tissues. Moreover, the splint 10 can be used as a brace for correcting or reorienting deformities of various portions of a patient's body. For example, patients with radial nerve damage ("wrist drop") can utilize the splint to reorient the affected hand to a natural position. Similarly, the splint 10 can be used to reorient hands deformed by osteoarthritis. Further, the splint 10 can be utilized to prevent or alleviate carpal tunnel syndrome.

While a preferred embodiment has been shown and described, it will be understood that there is no intent to limit the invention to such disclosure but rather it is intended to cover all modifications and alternate constructions falling within the spirit and scope of the invention as defined in the appended claims.

I claim:

1. A splint device for biasing a body portion of a patient to a preselected position and for at least partially immobilizing the body portion, said device comprising:

a splint body preformed to restrain the body portion in said preselected position, said splint body defining at least two ribs and at least two lateral portions which are interconnected, said at least two lateral portions for maintaining a relative position of said at least two ribs, said at least two ribs being configured to at least partially immobilize the body portion in said preselected position, said splint body integrally fabricated of a resilient material.

2. The splint device of claim 1 wherein said at least two ribs and said at least two lateral portions are interconnected in a manner such that a plurality of openings are defined each of which revealing a portion of the skin of the body portion.

3. The splint device of claim 1 wherein each of said at least two ribs defines a preselected thickness, when in an uncompressed state, to achieve a preselected degree of flexibility, said preselected thickness varying along a length and width of each of said at least two ribs.

4. The splint device of claim 1 wherein said resilient material defines a modulus of elasticity to achieve a preselected degree of flexibility.

5. The splint device of claim 1 wherein said resilient material defines a softening temperature such that said splint body is remoldable to an alternate preselected position.

6. The splint device of claim 1 wherein said resilient material is waterproof.

7. The splint device of claim 1 wherein said resilient material permits the passage of x-rays therethrough such that said splint device is wearable while the body portion is x-rayed.

8. The splint device of claim 1 wherein said device further comprises securing means for securing said splint body to the body portion of the patient.

9. The splint device of claim 8 wherein said securing means includes at least one strap integrally formed with said splint body.

10. The splint device of claim 1 wherein said splint body is configured to bias a wrist of the patient in said preselected position, said at least two ribs being positioned such that one rests on an ulnar side of the wrist and another rests of the radial side of the wrist such that a carpal tunnel region of the wrist is revealed.

11. The splint device of claim 1 wherein said splint body is configured to bias a foot of the patient in said preselected position.

12. The splint device of claim 1 wherein said splint body is configured to bias a finger of the patient in said preselected position.

13. The splint device of claim 1 wherein said splint body is configured to bias an elbow of the patient in said preselected position.

14. The splint device of claim 1 wherein said splint body is configured to bias a knee in the patient in said preselected position.

15. The splint device of claim 1 wherein said splint body is configured to bias the upper back of the patient in said preselected position.

16. The splint device of claim 15 wherein said splint body further defines a lumbar portion, a cervical portion and a thoracic portion, said lumbar portion receiving the lumbar region of the patient, said cervical portion supporting the back of the neck and head of the patient such that the neck and the head are biased in a correctly aligned position, said thoracic portion receiving the spinal column, said thoracic portion biasing the spinal column in a corrected position.

17. The splint device of claim 1 wherein said splint body is configured to encircle and support the neck of the patient.

18. The splint device of claim 17 wherein said splint body defines an extension for supporting the upper back of the patient.

19. The splint device of claim 1 wherein said splint body is configured to support the hips of the patient wherein the hips have a ball and a socket for each leg, said splint body configured to maintain the ball in the socket for each of the legs.

20. A splint device for biasing a body portion of a patient to a preselected position and for at least partially immobilizing the body portion, said device comprising:

a splint body preformed to restrain the body portion in said preselected position, said splint body defining at least two ribs and at least two lateral portions which are interconnected, said at least two lateral portions for maintaining a relative position of said at least two ribs, said at least two ribs being configured to at least partially immobilize the body portion in said preselected position, said at least two ribs and at least two lateral portions being interconnected in a manner such that a plurality of openings are defined each of which revealing a portion of the skin of the body portion, said splint body integrally fabricated of a resilient material, said resilient material being waterproof; and, a securing means for securing said splint body to the body portion of the patient.

21. The splint device of claim 20 wherein each of said at least two ribs defines a preselected thickness, when in an uncompressed state, to achieve a preselected degree of flexibility, said preselected thickness varying along a length and width of each of said at least two ribs.

22. The splint device of claim 20 wherein said resilient material defines a softening temperature such that said splint body is remoldable to an alternate preselected position.

23. The splint device of claim 20 wherein said resilient material permits the passage of x-rays therethrough such that said splint device is wearable while the body portion is x-rayed.

24. The splint device of claim 20 wherein said securing means includes at least one strap integrally formed with said splint body.

* * * * *